(12) United States Patent
Olson et al.

(10) Patent No.: US 6,358,718 B1
(45) Date of Patent: Mar. 19, 2002

(54) METHOD FOR STABILIZATION AND RENATURATION OF PROTEINS USING NUCLEOLAR PROTEIN B23

(75) Inventors: Mark Olson, Jackson; Atilla Szebeni, Brandon, both of MS (US)

(73) Assignee: The University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 09/538,871

(22) Filed: Mar. 30, 2000

Related U.S. Application Data

(60) Provisional application No. 60/126,910, filed on Mar. 30, 1999.
(51) Int. Cl.$^7$ .......................... C12N 9/96; C12N 21/20; C12N 11/00; C12N 15/12
(52) U.S. Cl. ...................... 435/183; 435/188; 435/69.1; 435/69.2; 435/68.1; 435/71.1; 435/71.2
(58) Field of Search ............................... 435/69.1, 69.2, 435/68.1, 188, 71.1, 71.2, 183

(56) References Cited

PUBLICATIONS

Craig E.A, Chaperones, Molecular in Molecular Biology biotechnology edited by Meyers R. A. 1995, pp. 162–165.*
Yon J. M, Protein Aggregation in, Molecular in Molecular Biology biotechnology edited by Meyers R. A. 1995, pp. 728–731.*
Borer et al., "Major Nucleolar Proteins Shuttle between Nucleus and Cytoplasma" *Cell* 56:379–390, Feb. 1989.
Chan et al., "Characterization of the cDNA Encoding Human Nucleophosmin and Studies of Its Role in Normal and Abnormal Growth" *Biochemistry* 28:1033–1039, 1989.
Fankhauser et al., "Specific Complex of Human Immunodeficiency Virus Type 1 Rev and Nucleolar B23 Proteins: Dissociation by the Rev Response Element" *Molecular and Cellular Biology* 11(5):2567–2575, May 1991.
Feuerstein et al., "Identification of a Prominent Nuclear Protein Associated with Proliferation of Normal and Malignant B Cells" *Journal of Immunology* 139(6):1818–1822, Sep. 15, 1987.
Goldfarb, D.S., "Karyophilic Peptides: Applications to the Study of Nuclear Transport" *Cell Biology International Reports*, 12(9):809–832, Sep. 1988.
Schmidt–Zachmann et al., "A Constitutive Nucleolar Protein Identified as a Member of the Nucleoplasmin Family" *The EMBO Journal*, 6(7):1881–1890, 1987.
Szebeni et al., "Interactions of Nucleolar Protein B23 with Peptides Related to Nuclear Localization Signals" *Biochemistry*, 34:8037–8042, 1995.
Szebeni et al., "Nucleolar Protein B23 Stimulates Nuclear Import of the HIV–1 Rev Protein and NLS–Conjugated Albumin" *Biochemistry*, 36(13):3941–3949, 1997.
Szebeni et al., "Molecular Chaperone–Like Activity of Nucleolar Protein B23" *FASEB Journal*, 12 (8) Abstract No. 636, May 16, 1998.
Szebeni, S., "Novel Biotechnological Applications of the Chaperone Like Activity of Protein B23" *Journal of the Mississippi Academy of Sciences*, 43(3):144–150, Jul., 1998.

* cited by examiner

*Primary Examiner*—Ali R. Salimi
*Assistant Examiner*—Bao Qun Li
(74) *Attorney, Agent, or Firm*—Needle & Rosenberg, P.C.

(57) ABSTRACT

The present invention provides methods for stabilizing proteins, preventing protein aggregation, renaturation of previously-denatured proteins, reactivating a protein that has been inactivated by denaturation, preserving enzyme activities under conditions of elevated temperatures, inducing thermotolerance in bacteria, increasing the temperature optimum for the activity of an enzyme, and preventing formation of inclusion bodies by bacterially-expressed recombinant proteins.

9 Claims, 29 Drawing Sheets

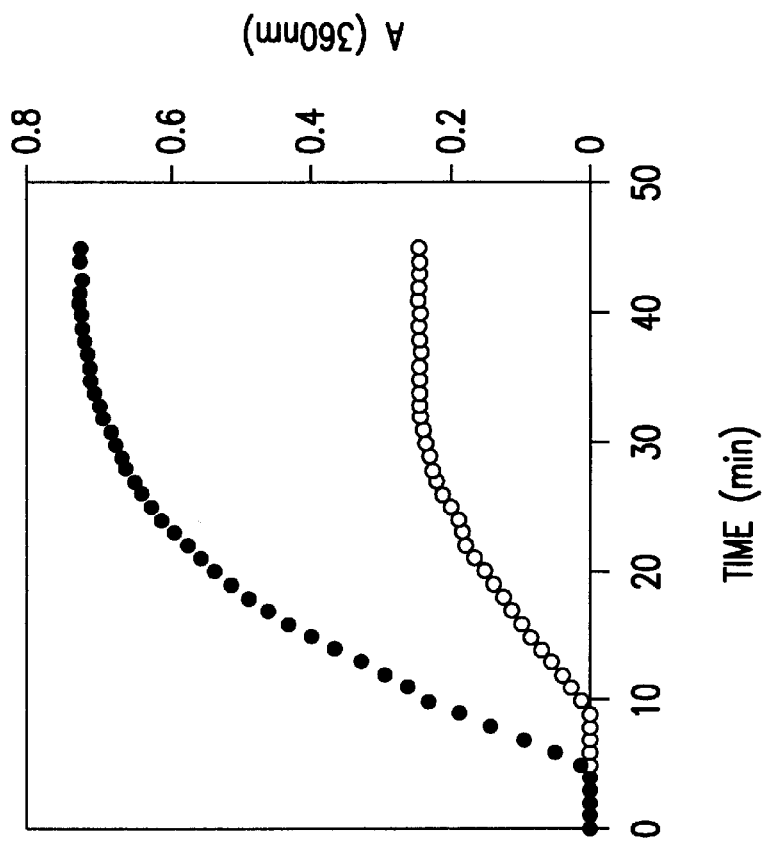
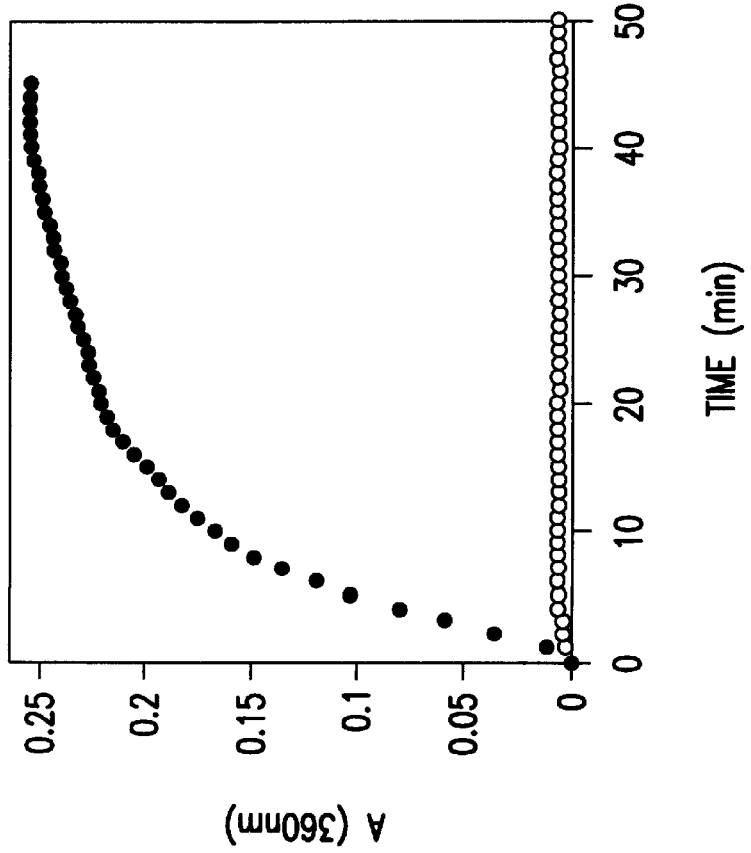
FIG.2A
FIG.2B

SEQUENCE LISTING

<160> NUMBER OF SEQ ID NOS: 4

<210> SEQ ID NO 1
<211> LENGTH: 1232
<212> TYPE: DNA
<213> ORGANISM: Artificial Sequence
<220> FEATURE:
<223> OTHER INFORMATION: Description of artificial sequence:/Note = synthetic construct

<400> SEQUENCE: 1

```
gttttccgtc cggcttctct cacactcaag tgcgcgcctc cacctcatgg aagactcgat      60
ggacatggac atgagccctc ttaggcctca gaactacctt ttcggttgtg aactaaaggc     120
tgacaaagat tatcacttta aagtggataa tgatgaaaat gagcaccagt tatcattaag     180
aacggtcagt ttaggagcag gggcaaaaga tgagttgcac atcgtagagg cagaagcaat     240
gaactatgaa ggcagcccaa ttaaagtaac actggcaact ttgaaaatgt ctgtacaacc     300
aacagtttcc cttgggggct tcgaaattac accacctgtg gtcttgaggt tgaagtgtgg     360
ttctgggcct gtgcacataa gtggacagca cctagtagct gtagaggaag atgcagagtc     420
agaagatgaa gatgaggaag atgtaaaact cttaggcatg tctggaaaga gatctgctcc     480
cggaggtggt aacaaagtcc cacagaaaaa agtaaaactt gatgaagatg atgatgagga     540
tgatgaagat gatgaggatg atgaagatga tgatgatgat gattttgatg aagaggaaac     600
tgaagaaaag gttccagtga gaaatctgt acgagatacc ccagccaaaa atgcacaaaa     660
atcaaaccaa aatgggaaag atttaaaacc atcaacacca aggtcaaagg gtcaagagtc     720
cttcaaaaaa caggaaaaaa ctcccaaaac acccaaagga cctagctctg tagaagacat     780
taaggcaaaa atgcaagcaa gtatagaaaa aggtggttct cttcccaaag tggaagccaa     840
gttcattaat tatgtgaaga attgtttccg gatgactgac caggaggcta ttcaagatct     900
ctggcagtgg aggaagtctc tttaagaaaa tggtttaaac agtttgaaat aattctgtct     960
tcatttctgt aatagttgct atctggctgt cctttttata atgcaaagtg agaactttcc    1020
ctactgtgtt tgataaatgt tgtccaggtt caattgccaa gaatgtgttg tctaaaatgc    1080
ctgtttagtt ttcaaggatg gaactccgcc ctttacttgg ttttaagtat gtatggaatg    1140
ttatgatagg acatagtagt agtggtggtc agatgtggaa atggtaggga gacaaatata    1200
catgtgaaat aaactcagta ttttaataaa gt                                  1232
```

<210> SEQ ID NO 2
<211> LENGTH: 292
<212> TYPE: PRT
<213> ORGANISM: Artificial Sequence
<220> FEATURE:
<223> OTHER INFORMATION: Description of artificial sequence:/Note = synthetic construct

<400> SEQUENCE: 2

```
Met Glu Asp Ser Met Asp Met Asp Met Ser Pro Leu Arg Pro Gln Asn
  1               5                  10                  15

Tyr Leu Phe Gly Cys Glu Leu Lys Ala Asp Lys Asp Tyr His Phe Lys
                 20                  25                  30

Val Asp Asn Asp Glu Asn Glu His Gln Leu Ser Leu Arg Thr Val Ser
             35                  40                  45

Leu Gly Ala Gly Ala Lys Asp Glu Leu His Ile Val Glu Ala Glu Ala
         50                  55                  60
```

```
Met Asn Tyr Glu Gly Ser Pro Ile Lys Val Thr Leu Ala Thr Leu Lys
 65                  70                  75                  80

Met Ser Val Gln Pro Thr Val Ser Val His Leu Gly Gly Phe Glu Ile
                 85                  90                  95

Thr Pro Pro Val Val Leu Arg Leu Lys Cys Gly Ser Gly Pro Ile Ser
            100                 105                 110

Gly Gln His Leu Val Ala Val Glu Glu Asp Ala Glu Ser Glu Asp Glu
        115                 120                 125

Asp Glu Glu Asp Val Lys Leu Leu Gly Met Ser Gly Lys Arg Ser Ala
    130                 135                 140

Pro Gly Gly Asn Lys Val Pro Gln Lys Lys Val Lys Leu Asp Glu
145                 150                 155                 160

Asp Asp Asp Glu Asp Glu Asp Asp Glu Asp Glu Asp Asp Asp
                165                 170                 175

Asp Asp Asp Phe Asp Glu Glu Glu Thr Glu Glu Lys Val Pro Val Lys
            180                 185                 190

Lys Ser Val Arg Asp Thr Pro Ala Lys Asn Ala Gln Lys Ser Asn Gln
        195                 200                 205

Asn Gly Lys Asp Leu Lys Pro Ser Thr Pro Arg Ser Lys Gly Gln Glu
    210                 215                 220

Ser Phe Lys Lys Gln Glu Lys Thr Pro Lys Thr Pro Lys Gly Pro Ser
225                 230                 235                 240

Ser Val Glu Asp Ile Lys Ala Lys Met Gln Ala Ser Ile Glu Lys Gly
                245                 250                 255

Gly Ser Leu Pro Lys Val Glu Ala Lys Phe Ile Asn Tyr Val Lys Asn
            260                 265                 270

Cys Phe Arg Met Thr Asp Gln Glu Ala Ile Gln Asp Leu Trp Gln Trp
        275                 280                 285

Arg Lys Ser Leu
    290

<210> SEQ ID NO 3
<211> LENGTH: 1164
<212> TYPE: DNA
<213> ORGANISM: Artificial Sequence
<220> FEATURE:
<223> OTHER INFORMATION: Description of artificial sequence:/Note =
      synthetic construct

<400> SEQUENCE: 3
gtgtctgttc tgcggaacag taggcagttg ttttccgtcc ggcttctctc acactcaagt      60
gcgcgcctcc acctcatgga agactcgatg acatgtgaca tgagccctct taggcctcag    120
aactaccttt tcggttgtga actaaaggct gacaaagatt atcactttaa agtggataat    180
gatgaaaatg agcaccagtt atcattaaga acggtcagtt taggagcagg ggcaaaagat    240
gagttgcaca tcgtagaggc agaagcaatg aactatgaag gcagcccaat taaagtaaca    300
ctggcaactt tgaaaatgtc tgtacaacca acagtttccc ttgggggctt cgaaattaca    360
ccacctgtgg tcttgaggtt gaagtgtggt tctgggcctg tgcacataag tggacagcac    420
ctagtagcta tagaggaaga tgcagagtca gaagatgaag atgaggaaga tgtaaaactc    480
ttaggcatgt ctggaaagag atctgctccc ggaggtggta acaaagtccc acagaaaaaa    540
gtaaaacttg atgaagatga tgatgaggat gatgaagatg atgaggatga tgaagatgat    600
gatgatgatg attttgatga agaggaaact gaagaaaagg ttccagtgaa gaaatctgta    660
```

-continued

```
cgagatacccc cagccaaaaa tgcacaaaaa tcaaaccaaa atgggaaaga tttaaaacca      720
tcaacaccaa ggtcaaaggg tcaagagtcc ttcaaaaaac aggaaaaaac tcccaaaaca      780
cccaaaggac ctagctctgt agaagacatt aaggcaaaaa tgcaagcaag tatagaaaaa      840
gcgcattgaa cattcctggg cactactggt aaattaagcc caaagatggg gaaagaggaa      900
aaggagaaac aaatatagta ccatcaacaa tccagactga agtcttctat tttaatctca      960 atccccttc ctgattggcc atccattccc ccttgcaggc tggaagcaat cgaaaaccta     1020
aagcattttt cttttccact cgggtgatgc agaaaacttg actgcttttc tataccactt     1080
gtgcatatgc cttaactctg accatgtttt aattttaacc tttgtatcct tagctgctcg     1140
aaataaattt ttgaatgaac caat                                            1164
```

<210> SEQ ID NO 4
<211> LENGTH: 257
<212> TYPE: PRT
<213> ORGANISM: Artificial Sequence
<220> FEATURE:
<223> OTHER INFORMATION: Description of artificial sequence:/Note = synthetic construct

<400> SEQUENCE: 4

```
Met Glu Asp Ser Met Asp Met Asp Met Ser Pro Leu Arg Pro Gln Asn
 1               5                  10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Asp Glu Glu Asp Val Lys Leu Leu Gly Met Ser Gly Lys Arg Ser Ala
    130                 135                 140

Pro Gly Gly Gly Asn Lys Val Pro Gln Lys Lys Val Lys Leu Asp Glu
145                 150                 155                 160

Asp Asp Asp Glu Asp Asp Glu Asp Asp Glu Asp Asp Glu Asp Asp Asp
                165                 170                 175

Asp Asp Asp Phe Asp Glu Glu Thr Glu Glu Lys Val Pro Val Lys
            180                 185                 190

Lys Ser Val Arg Asp Thr Pro Ala Lys Asn Ala Gln Lys Ser Asn Gln
        195                 200                 205

Asn Gly Lys Asp Leu Lys Pro Ser Thr Pro Arg Ser Lys Gly Gln Glu
    210                 215                 220

Ser Phe Lys Lys Gln Glu Lys Thr Pro Lys Thr Pro Lys Gly Pro Ser
225                 230                 235                 240

Ser Val Glu Asp Ile Lys Ala Lys Met Gln Ala Ser Ile Glu Lys Ala
                245                 250                 255

His
```

METHOD FOR STABILIZATION AND RENATURATION OF PROTEINS USING NUCLEOLAR PROTEIN B23

CROSS REFERENCE TO RELATED APPLICATIONS

This application claims the benefit, pursuant to 35 U.S.C. §119(e), of applicants' provisional U.S. patent application Ser. No. 60/126,910, filed Mar. 30, 1999, entitled "Methods For Stabilization And Renaturation Of Proteins Using Nucleolar Protein B23."

This invention was made with government support under NIH Grants AI34277 and GM28349. The government has certain rights in the invention.

BACKGROUND OF THE INVENTION

1. Field of the Invention

The present invention provides methods for stabilizing proteins, preventing protein aggregation, renaturation of previously-denatured proteins, reactivating a protein that has been inactivated by denaturation, preserving enzyme activities under conditions of elevated temperatures, inducing thermotolerance in bacteria, increasing the temperature optimum for the activity of an enzyme, and preventing formation of inclusion bodies by bacterially-expressed recombinant proteins.

2. Background Art

Technologies for the production of virtually any polypeptide by introduction, by recombinant DNA methods, of a natural or synthetic DNA fragment coding for this particular polypeptide into a suitable host have been under intense development over the past fifteen years, and are at present essential tools for biochemical research and for a number of industrial processes for production of high-grade protein products for biomedical or other industrial use.

The production of recombinant bioactive protein has become possible through developments in the field of recombinant DNA technology, but is often not successful in practice because frequently folding and/or secretion of the heterologous proteins that are to be produced does not occur correctly or occurs inefficiently. Such a problem usually occurs in cases of strong expression of the heterologous protein in a cell which has insufficient capacity to ensure correct folding or secretion of a protein that is produced in a large amount. The problem arises from the fact that recombinant proteins are produced in large amounts in prokaryotic cells or eukaryotic cells so that the activity of the cellular folding proteins is not sufficient for folding the huge amount of foreign protein.

A recombinant gene product which is foreign to the cell or is produced at high levels often activates cellular defense mechanisms similar to those activated by heat shock or exposure to toxic amino acid analogues, pathways that have been designed by nature to help the cell to get rid of "wrong" polypeptide material by controlled intracellular proteolysis or by segregation of unwanted polypeptide material into storage particles ("inclusion bodies"). The recombinant protein in these storage particles is often deposited in a misfolded and aggregated state, in which case it becomes necessary to dissolve the product under denaturing and reducing conditions and then fold the recombinant polypeptide by in vitro methods to obtain a useful protein product. Another problem is that proteins often tend to aggregate in solution. The formation of aggregates then causes loss in the activity of biologically active proteins or prevents the correct folding of unfolded or misfolded proteins by in vitro refolding methods.

In nature, correct folding of proteins produced by a cell is ensured by molecular chaperone proteins which are essential for correct functioning of cells as they ensure that proteins produced by the cells are folded in a correct manner. Specific chaperone proteins have been described for protein transport from the cell cytoplasm to cell organelles such as the mitochondrion, the chloroplast, the cell nucleus and the ER. The production of many of these proteins is induced in cells that are subjected to a heat shock and chaperone proteins are therefore often called "heat-shock proteins".

The present invention offers a solution to the problems of aggregation and formation of inclusion bodies, and also provides a means for increasing thermal tolerance of a protein (e.g., by stabilizing a thermolabile enzyme) and for preserving enzyme activity under denaturing conditions, in that methods are provided for the use of protein B23 as a chaperone in vitro or in vivo. The use of B23 as chaperone allows efficient production of proteins in a transformed host cell by co-expression of B23 with the desired, or by treating protein with B23 in vitro.

The present invention is based on the surprising discovery that B23 has a chaperone function which can be used in vitro or in vivo for deaggregation and prevention of aggregation of a protein, and in vivo for the efficient production of recombinant protein from a host cell if B23 and the recombinant protein are co-expressed in the cell.

SUMMARY OF THE INVENTION

In accordance with the purpose(s) of this invention, as embodied and broadly described herein, this invention, in one aspect, relates to a method of preventing protein aggregation of a selected protein, comprising contacting a solution containing the selected protein with the nucleolar protein B23, thereby promoting solubility of the selected protein.

In another embodiment, the invention provides a method of protecting a selected protein from aggregation during denaturation, comprising contacting the selected protein with the nucleolar protein B23 while subjecting the selected protein to at least one denaturing condition, thereby preventing aggregation of the selected protein.

The invention also provides a method of preserving enzyme activity of a selected enzyme, comprising contacting the selected enzyme with nucleolar protein B23.

In yet another embodiment, the invention provides a method of renaturing a denatured protein, comprising contacting the denatured protein with nucleolar protein B23 under conditions that promote renaturation of the denatured protein.

The invention also provides a method of inducing thermal tolerance in bacteria, comprising contacting the bacteria with the nucleolar protein B23.

In yet another embodiment, the invention provides a method of preventing the formation of inclusion bodies in recombinant protein-expressing bacteria, comprising promoting expression of the recombinant protein by the bacteria and contacting the newly expressed recombinant protein with nucleolar protein B23.

In yet another embodiment, the invention provides a method of stabilizing a thermolabile enzyme, comprising contacting the thermolabile enzyme with the nucleolar protein B23.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 2A–2D. Effect of protein B23 on the thermal denaturation of various substrate proteins. The proteins were subjected to thermal denaturation at the temperatures indicated below in the absence (●) or presence (○) of an equimolar concentration of protein B23.1 as described in the Examples. The turbidity was monitored at 360 nm. A: horse liver alcohol dehydrogenase (37° C.); B: bovine pancreatic carboxypeptidase A (48° C.); C: citrate synthase (43° C.); D: rhodanese (65° C.). All data are expressed as means of three experiments.

FIG. 4A: LADH; The dashed lines indicate relative activities between the 160 minute and 16 hour time points. FIG. 4B: rhodanese.

FIG. 7B shows the effect of protein B23 on the temperature-induced aggregation of green fluorescent protein at 75° C. as a function of time. FIG. 7C shows the effect of protein B23 on the temperature-induced aggregation of rhodanese at 60 and 82° C. as a function of time. FIG. 7D shows the effect of protein B23 on the temperature-induced aggregation of citrate synthase at 65° C. as a function of time. FIG. 7E shows the effect of protein B23 on the temperature-induced aggregation of liver alcohol dehydrogenase at 45° C. as a function of time.

FIG. 8A shows the effect of protein B23 on the time course of thermal denaturation on citrate synthase as measured by enzyme activity. FIG. 8B shows the effect of protein B23 on the time course of thermal denaturation of rhodanese as measured by enzyme activity. FIG. 8C shows the effect of protein B23 on the time course of thermal denaturation of liver alcohol dehydrogenase as measured by enzyme activity.

FIG. 9A shows the effect of protein B23 on the long-term stability of citrate synthase in solution at room temperature. FIG. 9B shows the effect of protein B23 on the long-term stability of liver alcohol dehydrogenase in solution at room temperature.

FIG. 10A shows the effect of protein B23 on the reactivation kinetics of chemically denatured liver alcohol dehydrogenase at 20° C. FIG. 10B shows the effect of protein B23 on the reactivation kinetics of chemically denatured rhodanese at 20° C.

FIG. 13A shows the effect of protein B23 on temperature-independent aggregation of HIV-1 Rev protein in a low ionic strength solution. FIG. 13B shows the effect of protein B23 on aggregation of CKII in a low ionic strength solution.

DESCRIPTION OF THE PREFERRED EMBODIMENTS

Figure 1A:
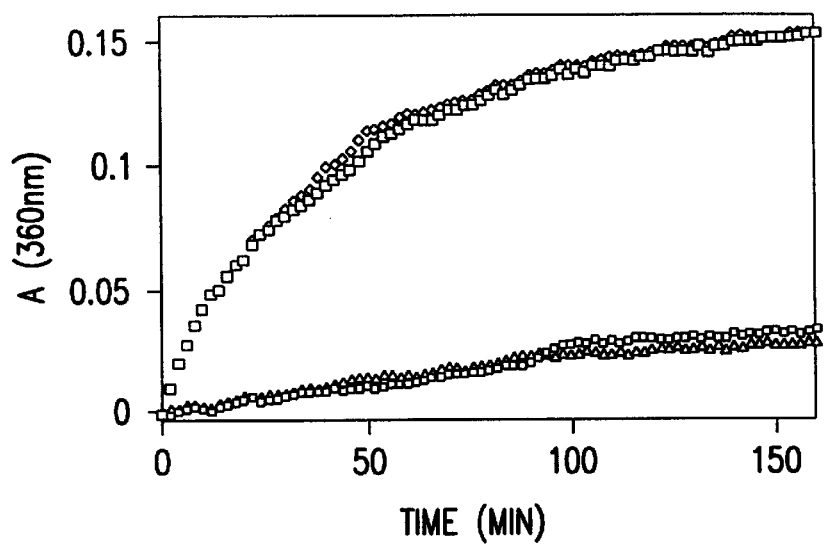
FIGS. 1A–1C. Chaperone activity of protein B23 against the HIV-1 Rev protein. A: Effect of protein B23 on temperature-dependent aggregation of the HIV1 Rev protein. Solutions of Rev protein (0.1 mg/ml in 50 mM phosphate buffer, pH 7.2, containing 150 mM NaCl, 1 mM DTT) without (□) or with equimolar amounts of added B23 (○, B23.1; △, B23.2) were allowed to warm from 4° C. to 28° C. in a semimicro cuvette. The Rev aggregation assay was also done in the presence of an equimolar concentration of BSA (◇). The turbidity was monitored at 360 nm as described in the Examples. B: Protein B23 concentration dependence of inhibition of Rev aggregation. Turbidity assays were performed as in panel A with increasing concentrations of protein B23.1. The % inhibition for each concentration of B23.1 was taken at the 20 minute time point. The data are shown as means of three determinations. C: Effect of protein B23 on temperature-independent aggregation of the Rev protein. Aliquots of Rev solution (0.5 mg/ml in 50 mM sodium phosphate buffer, pH 7.0, containing 150 mM NaCl, 200 mM KCl and 1 mM DTT) were dialyzed against 20 mM phosphate buffer (pH 7.0) containing 1 mM DTT at 4° C. The samples included increasing amounts of protein B23.1 as indicated by the ratios of Rev:B23. The turbidity was measured at 360 nm after overnight dialysis. Data are expressed as the percentage of the maximum turbidity (Rev without added protein B23). The data are shown as means of two determinations.

The present invention may be understood more readily by reference to the following detailed description of preferred embodiments of the invention and the Examples included therein and to the Figures and their previous and following description.

As used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As is indicated in the Examples, below, it has been discovered that protein B23 acts as a molecular chaperone to a wide variety of proteins including enzymes (carbonic anhydrase, alcohol dehydrogenase, rhodanese, casein kinase II, citrate synthase or pancreatic carboxypeptidase A) and nonezymatic proteins (green fluorescent protein, the HIV-1 Rev protein, or the amyloid beta protein). The activity operates at a broad range of temperatures, from as low as 4° C. (HIV-1 Rev) to as high as 80–82° C. (carbonic anhydrase or rhodanese). The chaperone activity does not depend on the size of the protein since relatively small proteins; e.g., the amyloid beta protein (MW 3262), are protected from aggregation as are relatively large proteins such as horse liver alcohol dehydrogenase (MW 39,805). Finally, the chaperone activity seems to be independent of the isoelectric point of the protein since it acts on basic substrates including alcohol dehydrogenase (pI 8.7) or acidic substrates such as carbonic anhydrase (pI 5.9).

Thus, the methods of the invention, which use protein B23 for stabilizing proteins, preventing protein aggregation, renaturation of previously-denatured proteins, reactivating a protein that has been inactivated by denaturation, preserving enzyme activities under conditions of elevated temperatures, inducing thermotolerance in bacteria, increasing the temperature optimum for the activity of an enzyme, and preventing formation of inclusion bodies by bacterially-expressed recombinant proteins, may be applied to any protein for which such beneficial results are desired. Furthermore, B23 can also be used in the methods of the invention for stabilizing proteins, preventing protein aggregation, renaturation of previously-denatured proteins, reactivating a protein that has been inactivated by denaturation, preserving enzyme activities under conditions of elevated temperatures, inducing thermotolerance in bacteria, increasing the temperature optimum for the activity of an enzyme, and preventing formation of inclusion bodies by bacterially-expressed recombinant proteins, where the protein in question is a protein-nucleic acid hybrid, or a protein that has been modified to include, e.g., carbohydrates.

Thus, for example, protein B23 could be used to stabilize enzymes used to manipulate nucleic acids, where it would be desirable to perform reactions at elevated temperatures in order to destabilize secondary structure in DNA or RNA. These reactions could include enzymes involving reverse transcriptases, DNA polymerases, phosphatases, restriction endonucleases, other exo- or endonucleases or ribonucleases. Protein B23 may also be used to stabilize these enzymes under conditions where alternating cycles of thermal denaturation and renaturation are used. In the case of these reactions it would be desirable to use the B23.2 isoform rather that B23.1, because the former does not bind nucleic acids.

It has been unexepectedly discovered that protein B23 can prevent the aggregation of a selected protein under a wide variety of conditions. Typically, B23 reduces aggregation of a protein by a percentage between 60% and 100%. The degree to which the aggregation of a given protein is reduced depends on the temperature used, the protein purity, the protein type, the protein concentration, and the B23:substrate ratio, as will be seen in the Examples below.

The present invention provides a method of preventing protein aggregation of a selected protein, comprising contacting a selected protein-containing solution with the nucleolar protein B23, thereby promoting solubility of the selected protein. The term "protein" refers to a polymer of amino acids and can include full-length proteins and polypeptides and fragments thereof. Solubility is maintained at high concentrations of the selected protein. By "high concentrations" is meant a concentration that, in the absence of a molecular chaperone protein such as nucleolar protein B23, would cause at least some of the selected protein to aggregate in the solution. An example of a high concentration would be concentrations generated in a protein expression system. The solution can be an aqueous solution and more specifically can be a physiological buffered solution.

The invention further provides the method of preventing substantial protein aggregation of a selected protein, wherein the selected protein is selected from the group consisting of HIV-1 Rev protein, liver alcohol dehydrogenase, carboxypeptidase A, citrate synthase, carbonic anhydrase, and rhodanese. Other proteins, however, could be selected, including, but not limited to, transcription enzymes, RNAses, ligases, replication enzymes, reverse transcriptases, and replicases.

"Nucleolar protein B23," as used herein, can include those proteins having slight variations in amino acid sequences or other properties of native nucleolar protein B23. Such variations may arise naturally as allelic variations (e.g., due to genetic polymorphism) or may be produced by human intervention (e.g., by mutagenesis of cloned DNA sequences), such as induced point, deletion, insertion and substitution mutants. When such variations occur, minor changes in amino acid sequence are generally preferred, such as conservative amino acid replacements, small internal deletions or insertions, and additions or deletions at the ends of the molecules. Substitutions may be designed based on, for example, the model of Dayhoff, et al., 1978. These modifications can result in changes in the amino acid sequence, provide silent mutations, modify a restriction site, or provide other specific mutations, so long as the modified protein shares at least one activity of the native protein. Confirmation of activity can be routinely provided following the methods described herein and elsewhere.

In a preferred embodiment, either of the two isoform of B23 (B23.1 and B23.2) are used in the methods of the invention. The nucleotide and amino acid sequence of B23.1 are set forth in SEQ ID NO:1 and SEQ ID NO:2, respectively, while the nucleotide and amino acid sequence of B23.2 are set forth in SEQ ID NO:3 and SEQ ID NO:4, respectively. Additional C-terminal truncated forms of B23 are contemplated in the present invention and can be used for the same purposes as laid out for B23.1 and B23.2.

The present invention also provides a method of protecting a selected protein from aggregation, and thus promoting solubility, during denaturation, comprising contacting the selected protein with the nucleolar protein B23 before or while subjecting the selected protein to at least one denaturing condition, thereby preventing aggregation of the selected protein. The denaturing condition can include, but is not limited to, thermal, chemical, or mechanical denaturation. The contacting step can preferably be in a solution whereby the solution contains both the selected protein and the nucleolar protein B23. The selected protein can be any protein. The protein can also be selected from enzymes, including, but not limited to, transcription enzymes, RNAses, ligases, replication enzymes, reverse transcriptases, replicases, kinases, and phosphatases. The selected protein can, more specifically, be selected from the group consisting of HIV-1 Rev protein, liver alcohol dehydrogenase, carboxypeptidase A, citrate synthase, carbonic anhydrase, and rhodanese.

Further provided is a method of preserving enzyme activity of a selected enzyme, comprising contacting the selected enzyme with nucleolar protein B23. Preferably, the contacting step is in a solution, and more preferably an aqueous solution, and even more preferably a physiological buffered solution. The selected enzyme can be any enzyme, including, but not limited to, transcription enzymes, RNAses, ligases, replication enzymes, reverse transcriptases, replicases, kinases, and phosphatases. The selected protein can, more specifically, be selected from the group consisting of HIV-1 Rev protein, liver alcohol dehydrogenase, carboxypeptidase A, citrate synthase, carbonic anhydrase, and rhodanese.

The present invention also provides a method of renaturing a denatured protein, comprising contacting the denatured protein with nucleolar protein thereby promoting renaturation of the denatured protein. The contacting step can be in a solution, and more preferably an aqueous solution, and even more preferably. The selected protein can be any protein. The protein can also be selected from enzymes, including, but not limited to, transcription enzymes, RNAses, ligases, replication enzymes, reverse transcriptases, replicases, kinases, and phosphatases. The selected protein can, more specifically, be selected from the group consisting of HIV-1 Rev protein, liver alcohol dehydrogenase, carboxypeptidase A, citrate synthase, carbonic anhydrase, and rhodanese.

The present invention also provides a method of reactivating a protein that has been inactivated by denaturation, comprising contacting the protein with nucleolar protein B23, thereby reactivating a protein that had been inactivated by denaturation. The contacting step can preferably be in a solution whereby the solution contains both the selected protein and the nucleolar protein B23. The selected protein can be any protein. The protein can also be selected from enzymes, including, but not limited to, transcription enzymes, RNAses, ligases, replication enzymes, reverse transcriptases, replicases, kinases, and phosphatases. The selected protein can, more specifically, be selected from the group consisting of HIV-1 Rev protein, liver alcohol dehydrogenase, carboxypeptidase A, citrate synthase, carbonic anhydrase, and rhodanese. The reactivation method may be used with proteins that have been inactivated by both thermal and chemical denaturation.

The invention also provides a method of increasing the temperature optimum for the activity of an enzyme, comprising contacting the enzyme with nucleolar protein B23, thereby increasing the temperature optimum for the activity of the enzyme. In one embodiment, the contacting step is in a solution, and more preferably an aqueous solution, and even more preferably a physiological buffered solution. In another embodiment, the contacting step is intracellular, and more preferably the nucleolar protein is provided intracellularly by genetically engineering the bacteria to express nucleolar protein B23. The bacteria can optionally be a recombinant protein-expressing bacteria, whereby the bacteria contains a vector that encodes a selected protein. The recombinant protein-expressing bacteria could also contain a vector for coexpressing a selected protein and nucleolar protein B23. The selected enzyme can be any enzyme, including, but not limited to, transcription enzymes, RNAses, ligases, replication enzymes, reverse transcriptases, replicases, kinases, and phosphatases. The selected protein can, more specifically, be selected from the group consisting of HIV-1 Rev protein, liver alcohol dehydrogenase, carboxypeptidase A, citrate synthase, carbonic anhydrase, and rhodanese.

Further provided is a method of inducing thermal tolerance in bacteria, comprising contacting the bacteria with the nucleolar protein B23, thereby increasing thermal tolerance of the bacteria. Preferably, the contacting step is intracellular, and more preferably the nucleolar protein is provided intracellularly by genetically engineering the bacteria to express nucleolar protein B23. These methods could be used to induce thermal tolerance in bacteria used in a bioreactor. One skilled in the art would recognize uses of methods to induce thermal tolerance whenever the desired function of the bacteria could be maximized at high temperatures. The bacteria can optionally be a recombinant protein-expressing bacteria, whereby the bacteria contains a vector that encodes a selected protein. The recombinant protein-expressing bacteria could also contain a vector for coexpressing a selected protein and nucleolar protein B23. The renaturation effect of B23 is seen in both thermal and chemical denaturation.

Also provided is a method of preventing the formation of inclusion bodies in recombinant protein-expressing bacteria, comprising promoting expression of the recombinant protein by the bacteria and contacting the expressed recombinant protein with nucleolar protein B23. Preferably, the contacting step is intracellular, and more preferably the nucleolar protein is provided intracellularly by genetically engineering the bacteria to express nucleolar protein B23. The recombinant protein-expressing bacteria can contain a vector that coexpresses a selected protein and nucleolar protein B23.

The present invention also provides a method of stabilizing a thermolabile enzyme, comprising contacting the thermolabile enzyme with the nucleolar protein B23. The stabilized thermolabile enzyme is used in nucleic acid applications, including, for example, a polymerase chain reaction. The stabilized thermolabile enzyme used in nucleic acid applications can include, for example, polymerases (like RNA polmerases T7, T6, T4, taq polymerase), transcription enzymes, ligases, replication enzymes (like Qb replicase), reverse transcriptases, or RNAses (such as, for example, Rnase H).

Also provided by the present invention is a vector for the coexpression of nucleolar protein B23 and a selected protein comprising nucleic acids that encode nucleolar protein B23 and at least one selected protein. The recombinant methodology for making vector and expressing the proteins is well known in the art. (See, e.g., Sambrook et al.) A nucleic acid encoding any selected protein can readily be made, based upon the genetic code, as known in the art. Nucleic acids can be obtained by any of several means known in the art. For example, cDNAs can be isolated from a library using a probe derived from the present nucleic acids or polypeptides, or nucleic acids can be directly synthesized mechanically. The nucleic acids can be double or single-stranded depending upon the purpose for which it is intended. Even more specifically, the vector can comprise a promoter functionally linked to the nucleic acids encoding nucleolar protein B23 and at least one selected protein. "Vector" means any carrier containing foreign DNA. "Vectors" include but are not limited to plasmids, viral nucleic acids, viruses, phage nucleic acids, phages, cosmids, and artificial chromosomes.

Also provided is a recombinant cell that expresses or overexpresses B23. The cell may be prokaryotic or eukaryotic. B23 may be expressed from a B23-encoding gene incorporated into a chromosome of the cell via recombination with the cell's chromosome, or may be expressed from a stably transfected vector.

The invention also provides a recombinant cell that expresses or overexpresses B23, and expresses or overexpresses a selected protein, where the selected protein may be endogenous or exogenous to the cell. The cell may be prokaryotic or eukaryotic. B23 may be expressed from a B23-encoding gene incorporated into a chromosome of the cell via recombination with the cell's chromosome, or may be expressed from a stably transfected vector. Similarly, the selected protein may be expressed from a gene encoding the protein that is incorporated into a chromosome of the cell via recombination with the cell's chromosome, or may be expressed from a stably transfected vector. Alternatively, the protein and B23 may be expressed from a vector which comprises both nucleolar protein B23 and a selected protein comprising nucleic acids that encode nucleolar protein B23 and the selected protein.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Proteins and Peptides—Recombinant proteins B23.1 and B23.2 used in these studies were produced in E. coli and purified essentially as previously described (Umekawa et al., 1993) except that the respective cDNAs were inserted into the pET11c vector (Novagen) for expression. The cDNA for the HIV-1 Rev protein was also inserted into pET11c and expressed in E. coli. The Rev protein was purified from crude extracts from E. coli as described previously (Karn et al., 1995) and refolded as described Wingfield et al. (1991).

Aggregation Assays with the Rev Protein—The Rev aggregation assay was based on the observation by Wingfield et al. (1991) that under certain conditions the protein aggregates when the temperature is raised from 0° C. to 28° C. The Rev protein was dissolved in 50 mM phosphate buffer containing 150 mM NaCl, 200 mM KCl, 1 mM DTT and 1 mM EDTA (pH 7.2) and the protein concentration was adjusted to 0.1 mg/ml. Ice-cold Rev solution was placed in a spectrophotometer cuvette and the temperature was raised from 4° to 28° C. over a two hour period, during which the absorbance was monitored at 360 nm. For the temperature-independent assay the Rev protein was dialyzed against 50 mM phosphate buffer containing 1 mM DTT (pH 7.2) at 4° C. in the presence or absence of equimolar quantities of protein B23. The turbidity was monitored at 360 nm over a period of several days.

Thermal denaturation of proteins—Freeze-dried horse liver alcohol dehydrogenase (LADH) was obtained from Fluka and used in an aggregation assay similar to that used with the Rev protein. The aggregation of LADH was monitored by measuring the apparent absorbance at 360 nm in a spectrophotometer at 37° C. Ice cold LADH solution (50 $\mu$g/ml in 20 mM Tris/HCl buffer, pH 7.4) with or without various concentrations of added protein B23 was placed in the cuvette and the turbidity was recorded automatically for one hour. Enzyme activity of LADH was assayed in 50 mM sodium phosphate buffer (pH 8.0) containing 0.2 mM NAD and 1 mM ethanol in a final volume of 1 ml and the rate of reduction of $NAD^+$ was monitored spectrophotometrically at 340 nm according to the method of (Guagliardi et al. 1995). Bovine pancreatic carboxypeptidase A (CPA) was obtained from Calbiochem as an aqueous crystalline suspension. The crystals were washed according to the instructions provided and then dissolved in 50 mM Tris/HCl (pH 7.5) containing 0.5 M NaCl. The protein concentration was determined with the Bio-Rad protein assay (Bradford, 1976.). Thermal aggregation of CPA was measured as above at 360 nm in a spectrophotometer cuvette held at 48° C. for up to 60 min. Porcine heart citrate synthase (Sigma) was subjected to thermal denaturation at 43° C., the course of which was followed by light scattering as described by Buchner et al.(1998).

Denaturation and refolding of LADH and Rhodanese—LADH was denatured for 20 min in 6 M guanidine-HCl in 0.1 M phosphate buffer (pH 7.6) containing 0.5 mM DTT and then separated from metal ions on a Sephadex G25 column equilibrated in 0.1 M phosphate buffer (pH 7.6) containing 6 M guanidine-HCl and 5 mM EDTA as described by Jaenicke and Rudolph (1990). The denatured protein fraction was used for refolding assays after 100-fold dilution with 0.1 M phosphate buffer (pH 7.6) containing 0.5 mM DTT and 3 $\mu$M $ZnCl_2$ at room temperature. Aliquots from the diluted mixture were used to measure the enzyme activity. Rhodanese activity during renaturation subsequent to guanidine HCl denaturation was measured essentially as described by Taguchi and Yoshida (1998).

Sucrose density gradient ultracentrifugation—Protein B23 was labeled with $^{125}I$ as previously described Szebeni and Olson (1997). Rhodanese (250 $\mu$g/ml) was incubated with an equimolar concentration of labeled protein B23 at room temperature or at 65° C. for 30 min in 50 mM Tris-HCl buffer (pH 7.8). After incubation the samples were layered onto 5–30% linear sucrose gradients in the same buffer and centrifuged in a Beckman SW41 rotor for 18 h at 38,000 RPM. Fractions (0.5 ml) were collected and the radioactivity of protein B23 and the enzyme activity of rhodanese were measured (see above).

ANS fluorescence measurements—Denaturation of rhodanese was carried out as described by Norcum (1996) with minor modifications. Rhodanese (2 mg/ml) in the presence or absence of protein B23 was denatured in guanidine HCl for 2 h at room temperature prior to taking the fluorescence measurements. The binding of the hydrophobic dye 1,8-ANS was measured using excitation at 390 nm and monitoring the fluorescence emission between 450 and 550 nm.

Protein B23 inhibits aggregation of the HIV-1 Rev Protein—The Rev protein undergoes reversible temperature-dependent or temperature-independent aggregation, depending on the conditions of ionic strength and sulfate concentration (Wingfield et al., 1991). To quantify the temperature-dependent aggregation we used a zero angle light scattering (turbidity) assay. The absorbance was monitored at 360 nm as the temperature rose from 0° C. to 30° C. in a spectrophotometer cuvette after adding ice-cold Rev solution. FIG. 1A shows that there was a relatively rapid aggregation phase over a period of 40–50 minutes followed by a gradual approach toward maximum turbidity within about 120 minutes. If the polymerized Rev protein was cooled again to 0° C., there was a slow disappearance of turbidity after approximately one day. In contrast, if an equimolar concentration of protein B23 was added to the Rev protein solution the rapid phase of the aggregation was prevented, although there was a slow increase in absorbance at 360 nm (FIG. 1A). When an equimolar concentration of BSA was used as a control, there was no effect on Rev protein aggregation. Protein B23 exists as two isoforms (Chang & Olson, 1990) with B23.2 containing 35 fewer amino acid residues at the C-terminal end compared to B23.1. To determine whether there were differences between the two isoforms in preventing Rev aggregation we did similar experiments using protein B23.2 instead of B23.1. FIG. 1A shows that the effects of the two isoforms on Rev aggregation were nearly identical, suggesting that the C-terminal end of B23.1 does not play a role in this activity.

Figure 1B:
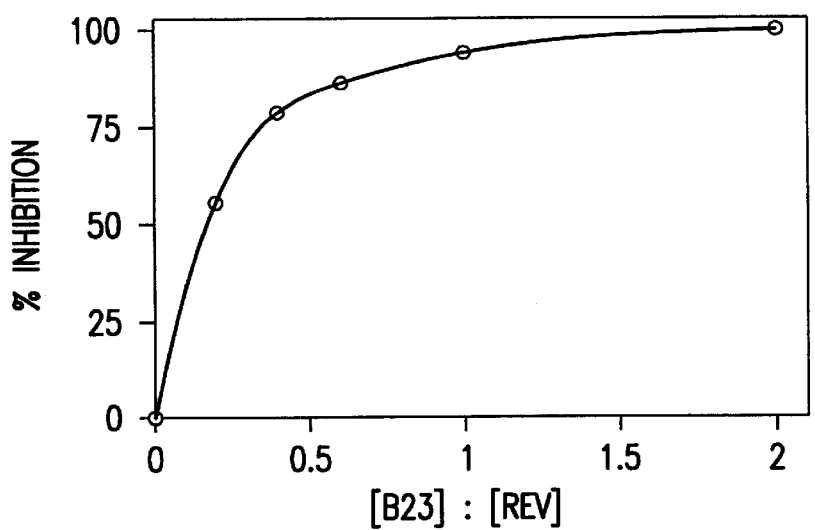

To determine the molar ratio for the maximum inhibition of Rev aggregation we repeated the assay as shown in FIG. 1A using various concentrations of protein B23.1. A separate curve was generated for each concentration of protein B23 and the % inhibition at the 20 minute time point was plotted versus the molar ratio of protein B23 to Rev (FIG. 1B). The inhibition of aggregation increased as the B23 concentration was raised, resulting in a hyperbolic curve. A plateau of inhibition of aggregation was seen when the molar ratio of B23:Rev was above one. Thus, under these conditions the Rev protein appears to form a relatively stable complex with protein B23, and the maximal effect appears to be achieved at a 1:1 stoichiometry between the two proteins.

Figure 1C:
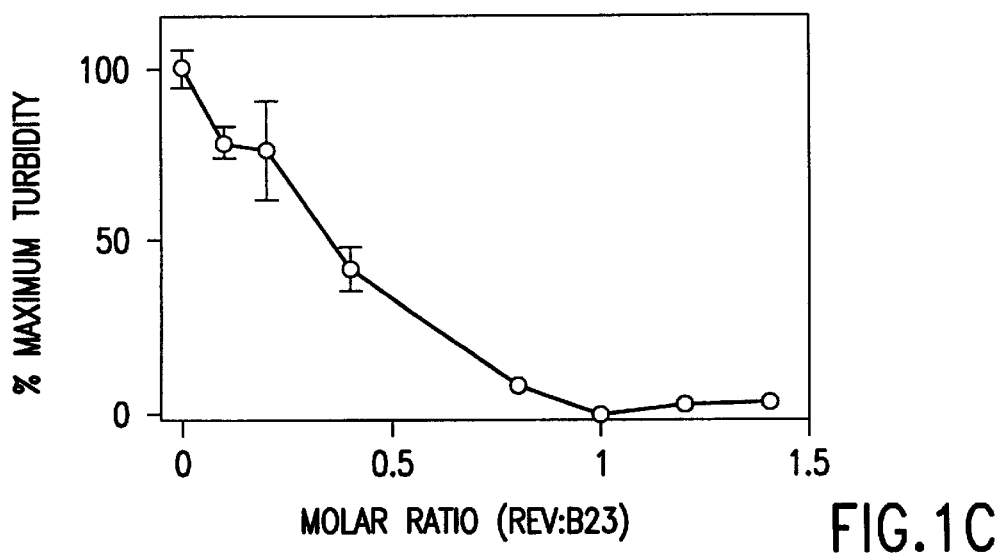

At low ionic strength the Rev protein undergoes a slow polymerization in a temperature-independent manner with formation of insoluble fibrous material (Wingfield et al., 1991). To test whether protein B23 also inhibited the temperature-independent polymerization of Rev, aliquots of Rev in high ionic strength buffer (approximately 400 mM) were dialyzed in micro dialyzer cassettes against low ionic strength buffer (20 mM) at 4° C. The samples included various concentrations of protein B23.1. The turbidity was measured as above after overnight dialysis. The samples containing Rev alone showed the greatest level of turbidity, whereas addition of increasing concentrations of protein B23 resulted in decreasing turbidity (FIG. 1C). As with the temperature-dependent aggregation described above the solutions were essentially clear when the B23:Rev ratio was greater than one. The Rev protein also has a tendency to polymerize and form filaments over a period of several days at 0–4° C., when its concentration is 1–2 mg/ml and under moderate ionic strength conditions (Wingfield et al., 1991). Addition of protein B23 also completely prevented this time-dependent Rev polymerization. Thus, the ability of protein B23 to inhibit Rev aggregation can be seen under several different conditions of ionic strengths and temperature.

Figure 2D:
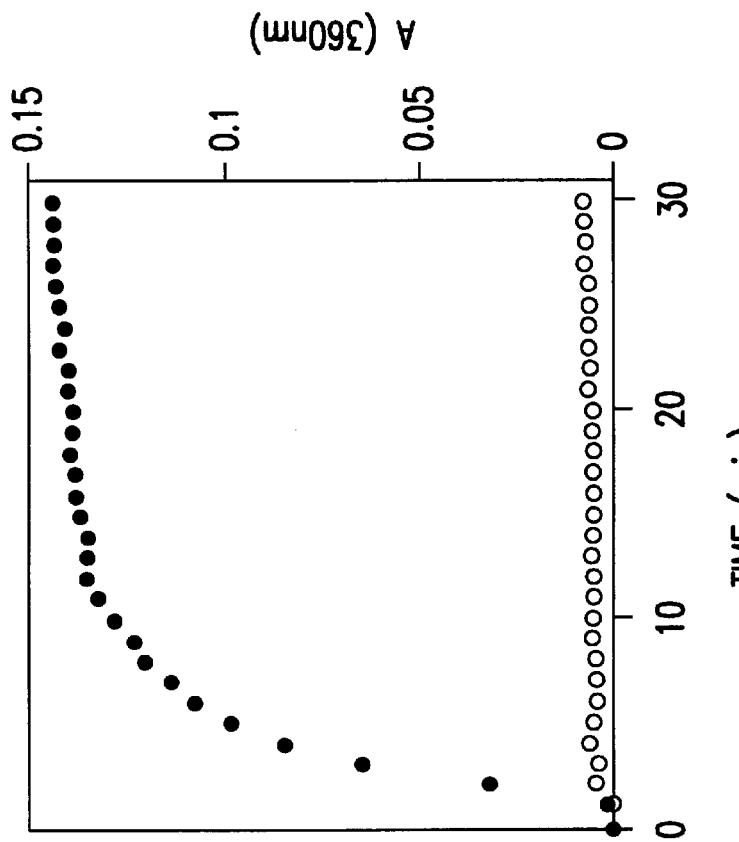

Protein B23 protects several proteins against thermal denaturation—The above studies provided evidence that protein B23 has chaperone-like activity toward a protein with which it is known to interact. To determine whether the protein has general chaperone activity we studied the effect of protein B23 on the thermal denaturation of four enzymes that have previously been used as substrates for chaperones; liver alcohol dehydrogenase (LADH), carboxypeptidase A (CPA), citrate synthase (CS) and rhodanese. Light scattering measurements showed that at a concentration of 100 $\mu$g/ml LADH aggregated when the temperature was increased from 0 to 37° C. reaching maximum turbidity in about 40 min (FIG. 2A). However, when a 1:1 molar ratio of protein B23 was added to the incubation medium containing LADH, the aggregation was nearly completely prevented. The protein B23.2 isoform showed the same antiaggregation effect on LADH as did B23.1, again suggesting that the C-terminal end of protein B23.1 does not play role in the chaperone activity. In control experiments, the presence of excess bovine serum albumin did not prevent the increases in light scattering.

Figure 2C:
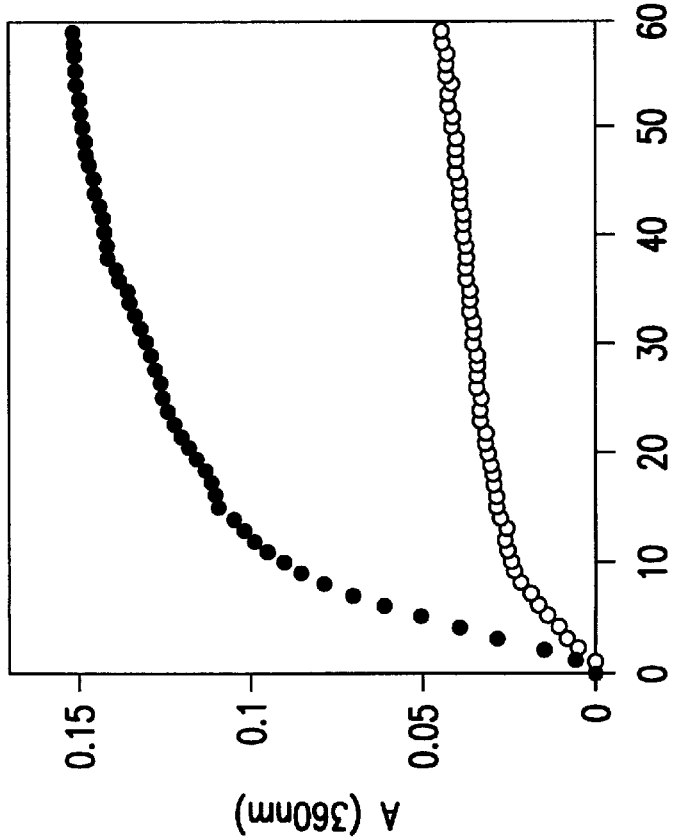
Figure 3:
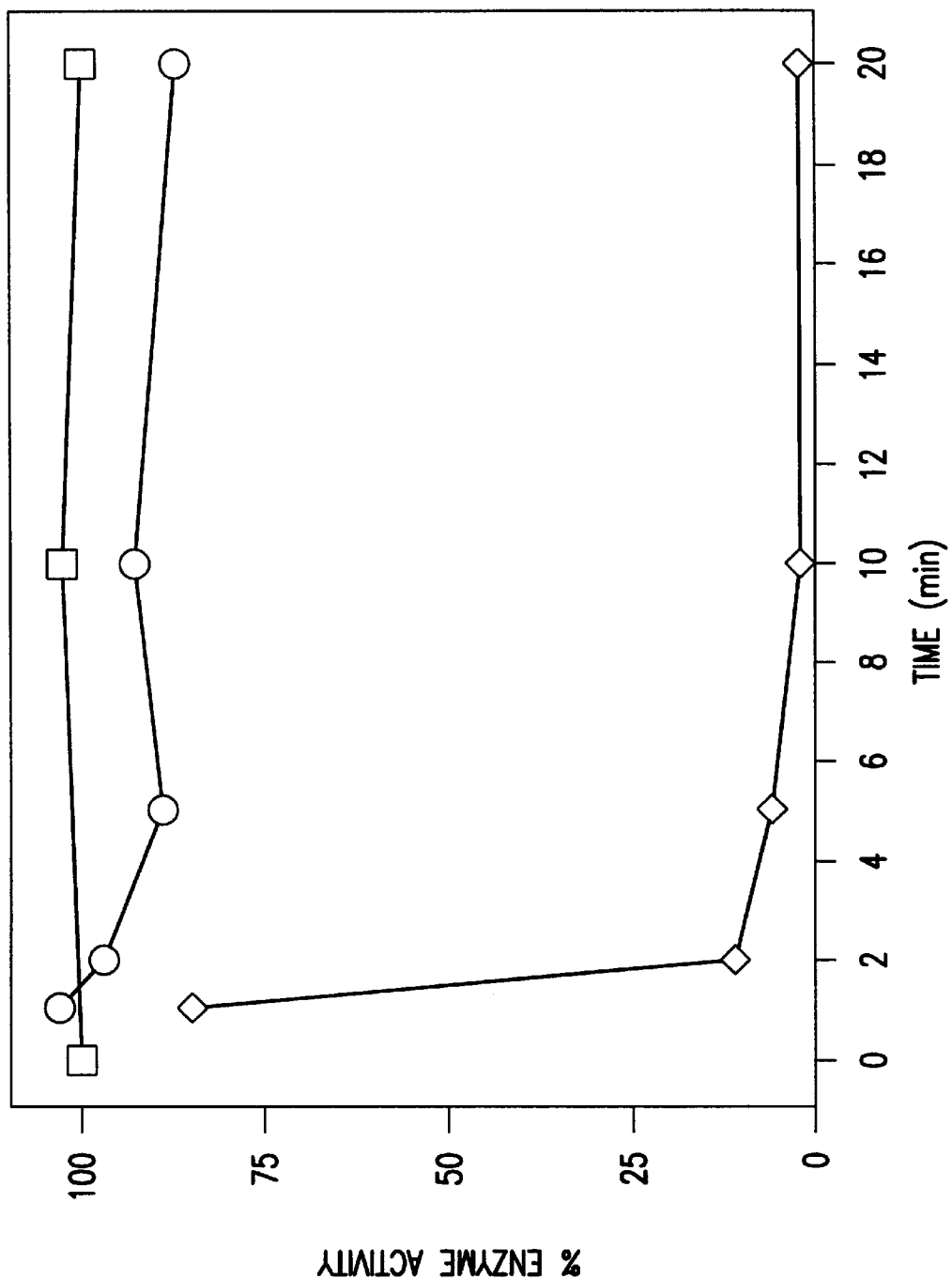
FIG. 3. Effect of Protein B23 on the enzyme activity of liver alcohol dehydrogenase during thermal denaturation. LADH was incubated at 50° C. in the presence (○) or absence (◇) of protein B23.1 at a molar ratio of 1:1 (B23:LADH). A LADH control without added protein B23.1 was kept at 22° C. (□). The enzyme activities were assayed as described below in the Examples. All data represent the means of three experiments.

Similar analyses were performed on the other three enzymes; the results were generally very similar to those obtained with LADH when stoichiometric amounts of protein B23.1 was present during denaturation. However, with CPA (FIG. 2B) and CS (FIG. 2C) only partial inhibition of aggregation was achieved at the 1:1 stoichiometry. On the other hand, complete protection against aggregation was obtained under these conditions with rhodanese. In control experiments, the presence of an equimolar concentration of BSA, did not alter the magnitude of aggregation Enzyme activity is a more sensitive measure of the native or denatured state of a protein than the aggregation assay. FIG. 3 shows the effect of protein B23 on the time course of thermal denaturation of LADH as measured by enzyme activity. LADH was incubated at 50° C. in the absence or presence of the protein B23.1 isoform at a molar ratio of 1:1 (B23:LADH). During heating, LADH lost enzyme activity very rapidly; i.e. within two minutes. However, when protein B23 was present the enzyme retained nearly complete activity. In control experiments it was found that the addition of B23 to an untreated solution of LADH did not influence the specific activity of the enzyme, nor did the presence of BSA protect the activity of LADH under the conditions used. Thus, protein B23 preserves the activity of LADH under high temperature conditions.

Protein B23 promotes the renaturation of chemically denatured proteins—Many molecular chaperones not only protect proteins against the effects of elevated temperatures, but they are also capable of promoting the refolding of denatured proteins. Two substrates, LADH and rhodanese were used to test for this possible activity in protein B23.

Figure 4A:
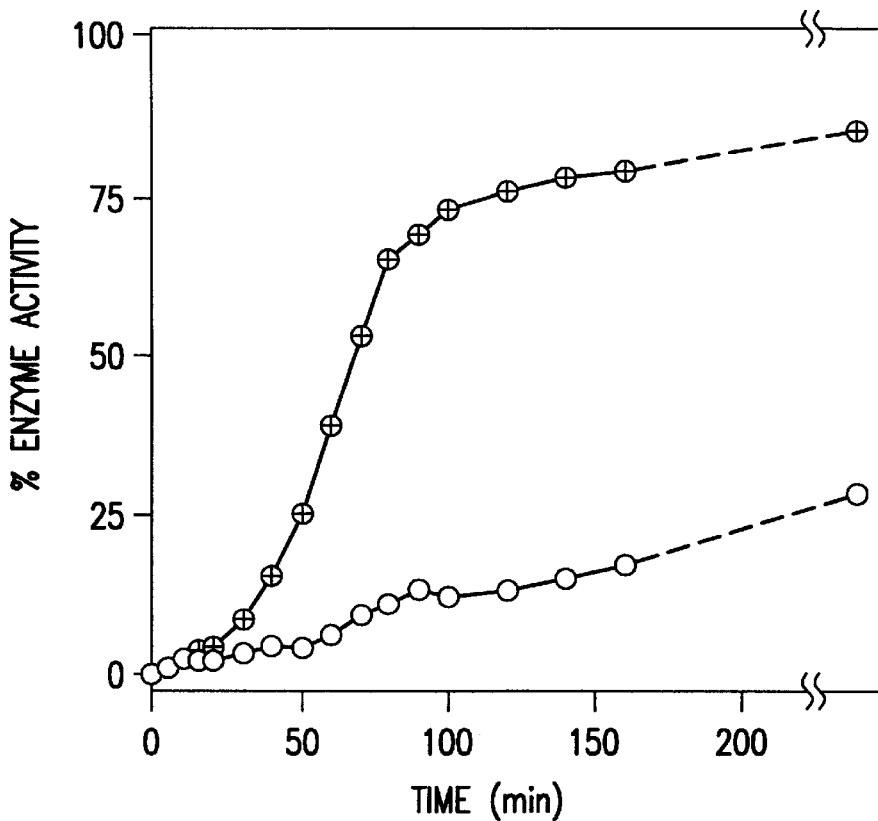
FIGS. 4A–4B. Protein B23 promotes the renaturation of chemically denatured liver alcohol dehydrogenase and rhodanese. Renaturation was done in the absence (○) or presence (⊕) of equimolar quantities of B23.1 as described in the Examples.

LADH was denatured in 6 M guanidine hydrochloride and diluted 100-fold as described above. The catalytic activity of the enzyme was measured after refolding in the absence or presence of protein B23 at a molar ratio of 1:1 (B23:LADH). FIG. 4A shows the time course of reactivation of LADH by protein B23. The enzyme was completely inactive after denaturation and dilution although there was a very slow restoration of the activity after several hours at room temperature. However, when B23 was present, 76% of the original activity was regained after 3 hours, compared to only about 20% in the untreated sample. In control experiments it was found that the addition of B23 to a native solution of LADH did not influence the specific activity of the enzyme. Furthermore, addition of BSA to the renaturing solution did not accelerate the recovery of enzyme activity.

Figure 4B:
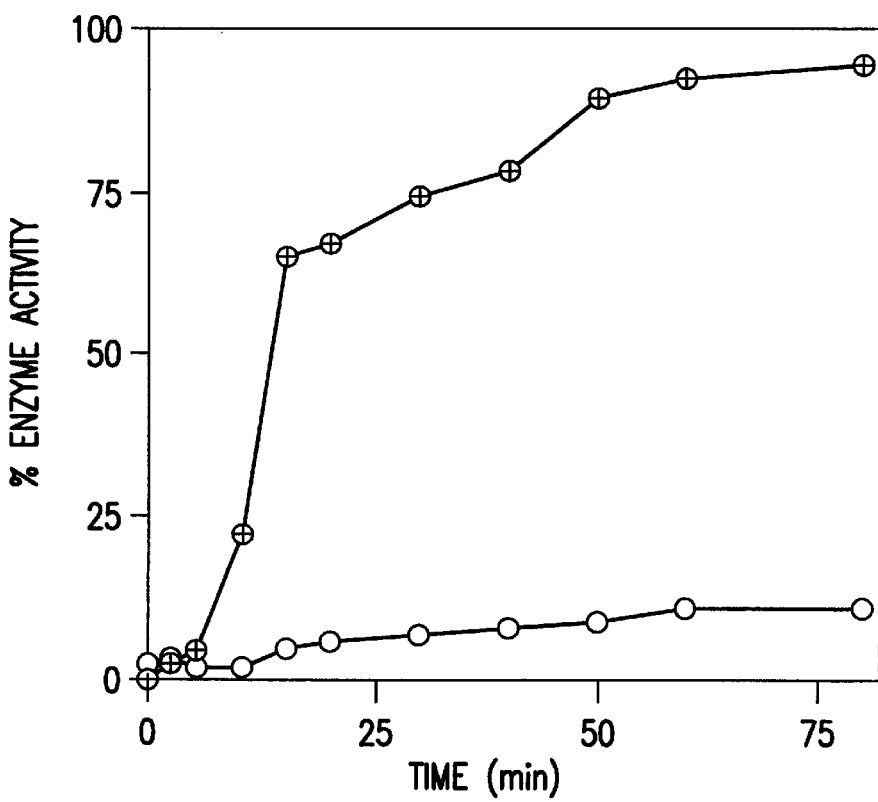

Similar results were obtained when rhodanese was used as a substrate for renaturation (FIG. 4B). In this case only about 10% of the original activity was regained 80 minutes after dilution of the guanidine HCl in the absence of protein B23. However, the enzyme recovered more than 95% of its activity when incubated with an equimolar quantity of protein B23 for 80 min at room temperature. Thus, protein B23 not only prevents aggregation and protects catalytic activity but it is also able to promote the renaturation of denatured proteins.

Figure 5A:
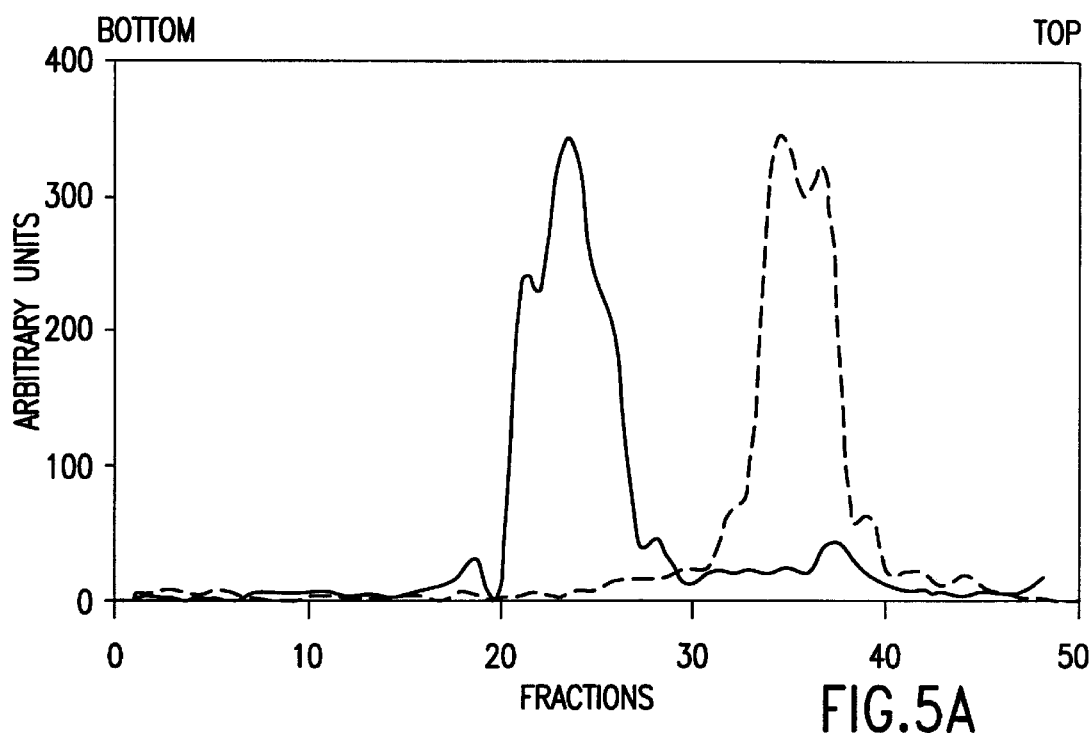
FIGS. 5A–5B. Sedimentation analysis of $^{125}$I labeled protein B23-rhodanese complexes. Equimolar mixtures of protein B23 and rhodanese were subjected to sucrose density gradient sedimentation as described in the Materials and Methods section before (A) or after (B) after 60 min of thermal denaturation at 65° C. The radioactivity of $^{125}$I-labeled protein B23 (solid line) and enzyme activity of rhodanese (dotted line) are indicated.
Figure 5B:
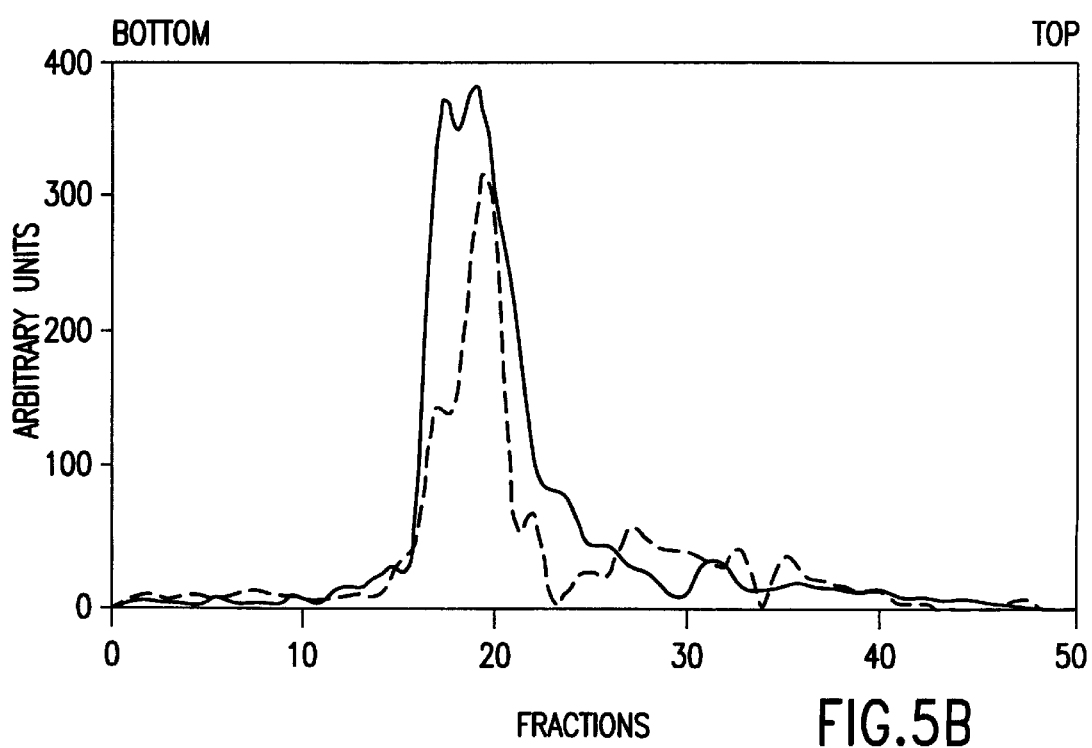

Protein B23 preferentially binds denatured substrates— Molecular chaperones generally prefer to bind denatured substrates. To test this possibility, the interaction of protein B23 with native or heat-denatured rhodanese was studied by sedimentation analyses. Samples of protein B23 labeled with $^{125}$I were mixed with equimolar quantities of rhodanese and then heated at 65° for 60 min. The heated samples and unheated control samples were subjected to analyses by sucrose density gradient centrifugation. FIG. 5A shows that under native conditions there was no interaction between rhodanese and protein B23. However, when the heated mixture was analyzed under the same conditions, the two proteins sedimented together and the enzyme activity of rhodanese was preserved. In control experiments it was found that when rhodanese was heated under the above conditions in the absence of protein B23 no enzyme activity was retained and the protein became insoluble which precluded its analysis by sedimentation. On the other hand, when protein B23 was heat-treated under the same conditions its sedimentation profile was nearly identical to that of the untreated sample. Similar experiments were performed with carbonic anhydrase, with essentially the same results. Thus, protein B23 appears to preferentially bind denatured proteins.

Figure 6:
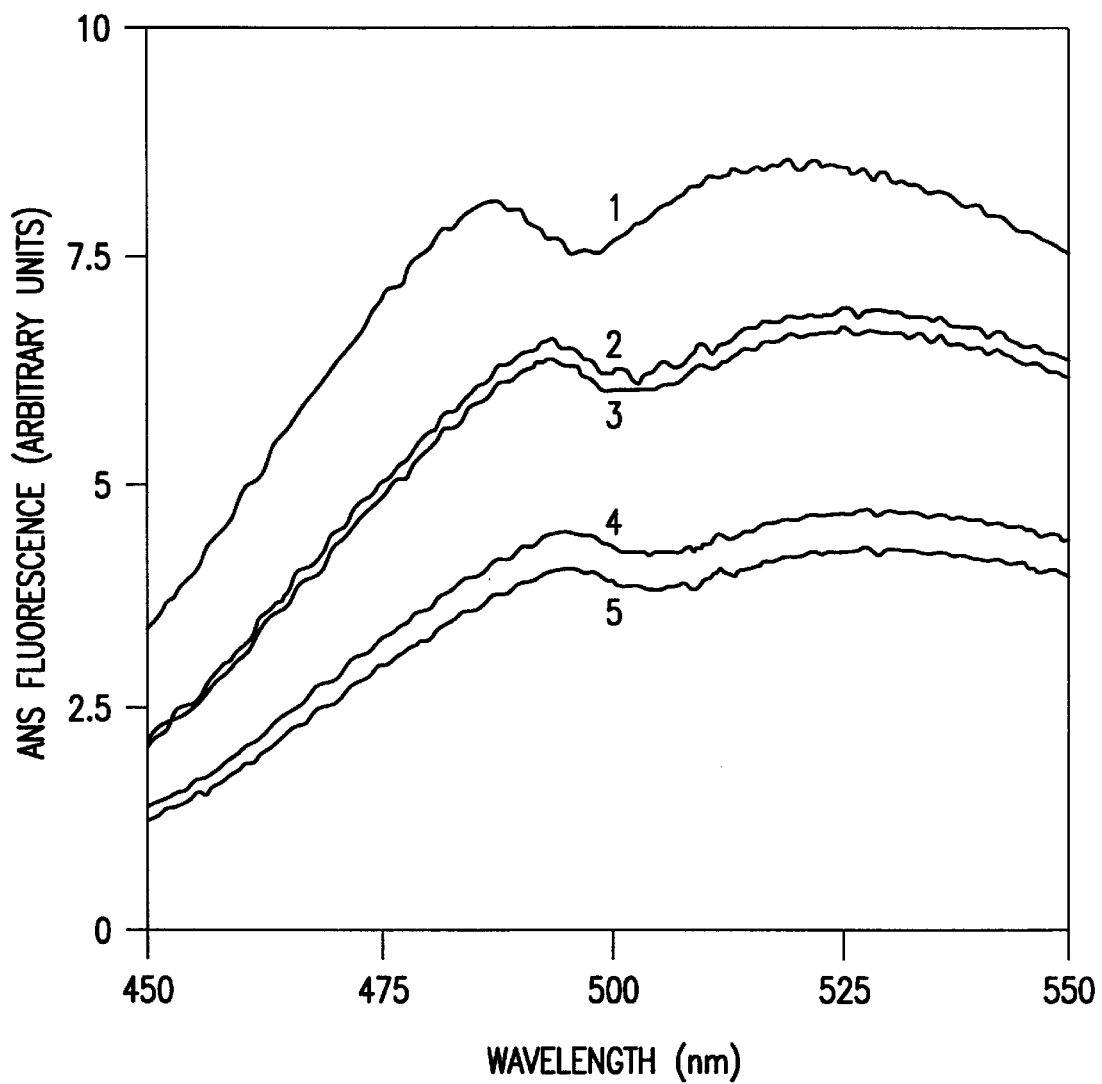
FIG. 6. ANS fluorescence emission spectra of protein B23-substrate complexes. The curve numbers indicate the samples which contained: equimolar concentrations of B23 and denatured rhodanese (1), equimolar concentrations of B23 and native rhodanese (2), B23 alone (3), denatured rhodanese alone (4) or native rhodanese alone (5). Curves shown are the average of three emission spectra with excitation at 390 nm.

Hydrophobic regions are exposed in the B23-substrate complex—Compounds based on anilinonaphthalene have increased fluorescence when placed in nonpolar environments, enabling them to be used as probes for hydrophobic regions induced by molecular chaperones (Martin et al. 1991; Mock et al., 1988). To test the possibility that hydrophobic regions are exposed when protein B23 interacts with a denatured substrate, the fluorescence of 1-anilino-8-sulfonate (ANS) was monitored during the interaction of B23 with rhodanese under various conditions. FIG. 6 shows that there were only small differences in the fluorescence spectra of ANS in the presence of native or denatured rhodanese. The ANS spectra were also similar when taken in the presence of protein B23 with or without added native rhodanese (FIG. 6, curves 2 and 3). However, there was a major increase in fluorescence and a shift toward lower wavelengths when a complex was formed between denatured rhodanese and protein B23 (FIG. 6, curve 1). The ANS fluorescence spectrum in the presence of B23 and denatured rhodanese was stable for several hours, suggesting that the altered conformation was maintained as long as the complex was not dissociated. Thus, the formation of the complex between denatured rhodanese and protein B23 induces conformational changes resulting in the exposure of hydrophobic regions in one or both of the proteins.

EXAMPLE 2

Sources of protein B23—Recombinant proteins B23 (the B23.1 isoform) was produced in bacteria using the pET expression vectors and purified as previously described (Wang et al., 1994).

Thermal denaturation of several proteins—Carbonic anhydrase was dissolved in 50 mM Tris/HCl buffer (pH 7.5) and the turbidity was monitored at 360 nm in a temperature controlled spectrophotometer cuvette at 80° C.

The Green Fluorescent Protein (GFP) was dissolved in 10 mM Tris/HCl buffer (pH 7.4) and the turbidity was monitored at 360 nm in a temperature controlled spectrophotometer cuvette at 75° C. The protein concentration was determined with the Bio-Rad protein assay.

Rhodanese (Sigma) was subjected to thermal denaturation at 60 and 82° C. in 10 mM Tris/HCl buffer (pH 7.4) and the turbidity was monitored at 360 nm in a temperature controlled spectrophotometer cuvette.

Porcine heart citrate synthase (Sigma St. Louis, Mo.) was subjected to thermal denaturation at 65° C., the course of which was followed by light scattering as described by Buchner et al.(1998).

Freeze-dried horse liver alcohol dehydrogenase (LADH) was obtained from Fluka (Buchs, Switzerland) and used in an aggregation assay. The aggregation of LADH was monitored by measuring the apparent absorbance at 360 nm in a spectrophotometer at 45° C. Ice cold LADH solution (50 μg/ml in 20 mM Tris/HCl buffer, pH 7.4) with or without various concentrations of added protein B23 was placed in the cuvette and the turbidity was recorded automatically for 50 minutes.

Chemical denaturation and refolding of LADH—LADH was denatured for 20 min in 6 M guanidine-HCl in 0.1 M phosphate buffer (pH 7.6) containing 0.5 mM dithiothreitol (DTT) and then separated from metal ions on a Sephadex G25 column equilibrated in 0.1 M phosphate buffer (pH 7.6) containing 6 M guanidine-HCl and 5 mM ethylenediamine tetraacetic acid (EDTA) as described by Jaenicke and Rudolph (1990). The denatured protein fraction was used for refolding assays after 100-fold dilution with 0.1 M phosphate buffer (pH 7.6) containing 0.5 mM DTT and 3 μM $ZnCl_2$ at room temperature. Aliquots from the diluted mixture were used to measure the enzyme activity.

Denaturation and refolding of rhodanese—Rhodanese activity during renaturation subsequent to guanidine HCl denaturation was measured essentially as described by Taguchi and Yoshida (1998). The final concentration of rhodanese was 50 μM during the renaturation experiment.

Determination of LADH activity—Enzyme activity of LADH was assayed in 50 mM sodium phosphate buffer (pH 8.0) containing 0.2 mM nicotinamide adenine dinucleotide (NAD) and 1 mM ethanol in a final volume of 1 ml and the rate of reduction of $NAD^+$ was monitored spectrophotometrically at 340 nm according to the method of (Guagliardi et al. (1995).

Determination of Carboxypeptidase A Activity—Bovine pancreatic carboxypeptidase A (CPA) was obtained from Calbiochem as an aqueous crystalline suspension. The crystals were washed according to the instructions provided and then dissolved in 50 mM Tris/HCl (pH 7.5) containing 0.5 M NaCl. The protein concentration was determined with the Bio-Rad protein assay (Bradford, 1976.). Thermal aggregation of CPA was measured as above by apparent absorbance at 360 nm in a spectrophotometer cuvette held at 48° C. for up to 60 min. Enzyme activities of CPA were determined spectrophotometrically at 254 nm, using 1 mM hippuryl-DL-phenylalanine as peptide substrate in 50 mM Tris/HCl buffer (pH 7.5) containing 0.5 M NaCl (Anson & Schirmer, 1963).

Protein phosphorylation—Recombinant B23 was phosphorylated with casein kinase II (Boehringer-Mannheim) under the reaction conditions described below. For casein kinase II phosphorylation (CKII) samples of protein B23 (0.3 mg/ml) were incubated in a reaction mixture containing 1 mU/ml CKII, 20 mM MES buffer (pH 7.2), 130 mM KCl, 0.4 mM $MgCl_2$, 48 mM DTT, 100 µM ATP, in a total volume of 1 ml at 25° C. for 30 min. After phosphorylation the samples were dialyzed in microdialysis flow cells against 20 mM HEPES buffer (pH 7.4). Aliquots (50 µl) from the incubation mixtures supplemented with γ-[$^{32}$P]ATP were routinely used to measure the efficiency of the enzyme reactions and to estimate the number of phosphoryl groups incorporated. The phosphorylation reaction was terminated by addition of 10% trichloroacetic acid (TCA) followed by 2 more washes in 10% TCA, with subsequent washes with methanol and ether. The radioactivity incorporated into the protein was measured in a liquid scintillation counter. The number of phosphoryl groups incorporated into the protein was calculated from the radioisotope incorporation, the specific activity of the γ-[$^{32}$P]ATP and the amount of protein as determined by the Bio-Rad protein assay.

Preparation of $^{125}$I-labeled protein—The protein B23 used for sucrose density gradient sedimentation were labeled with $^{125}$I using IODOGEN as described by the manufacturer (Pierce Chemical Co.). The labeled protein was separated from the free $^{125}$I by a Sephadex G-25 column. The concentrations and specific activities of the $^{125}$I-labeled proteins were determined by absorbance at 280 nm. Radioactivity was measured in a gamma counter.

I. Protein B23 Prevents the Aggregation of Proteins Under Elevated Temperature Conditions Several proteins were subjected to thermal denaturation at various temperatures as indicated in the presence or absence of protein B23 in an equimolar ratio to substrate. The turbidity was monitored at 360 nm.

Figure 7A:
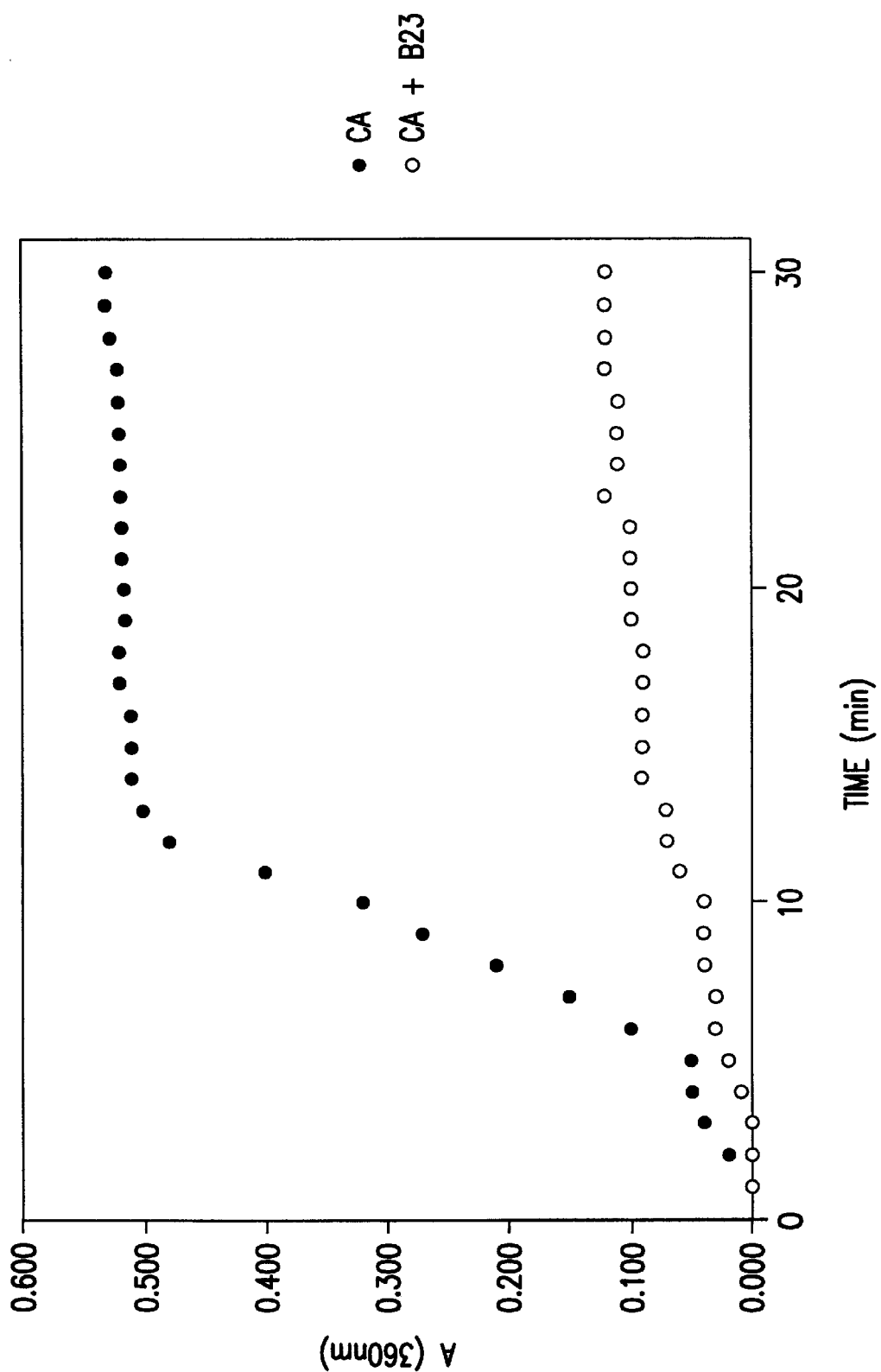
FIGS. 7A–7E are graphs showing the effect of protein B23 on the temperature-induced aggregation of various proteins. 7A shows the effect of protein B23 on the temperature-induced aggregation of carbonic anhydrase at 80° C. as a function of time.

The effect of protein B23 on the thermal denaturation of Carbonic anhydrase at 80° C. is shown in FIG. 7A. Carbonic anhydrase (80 µg/ml) was subjected to thermal denaturation in the absence or presence of an equimolar concentration of protein B23.

Figure 7B:
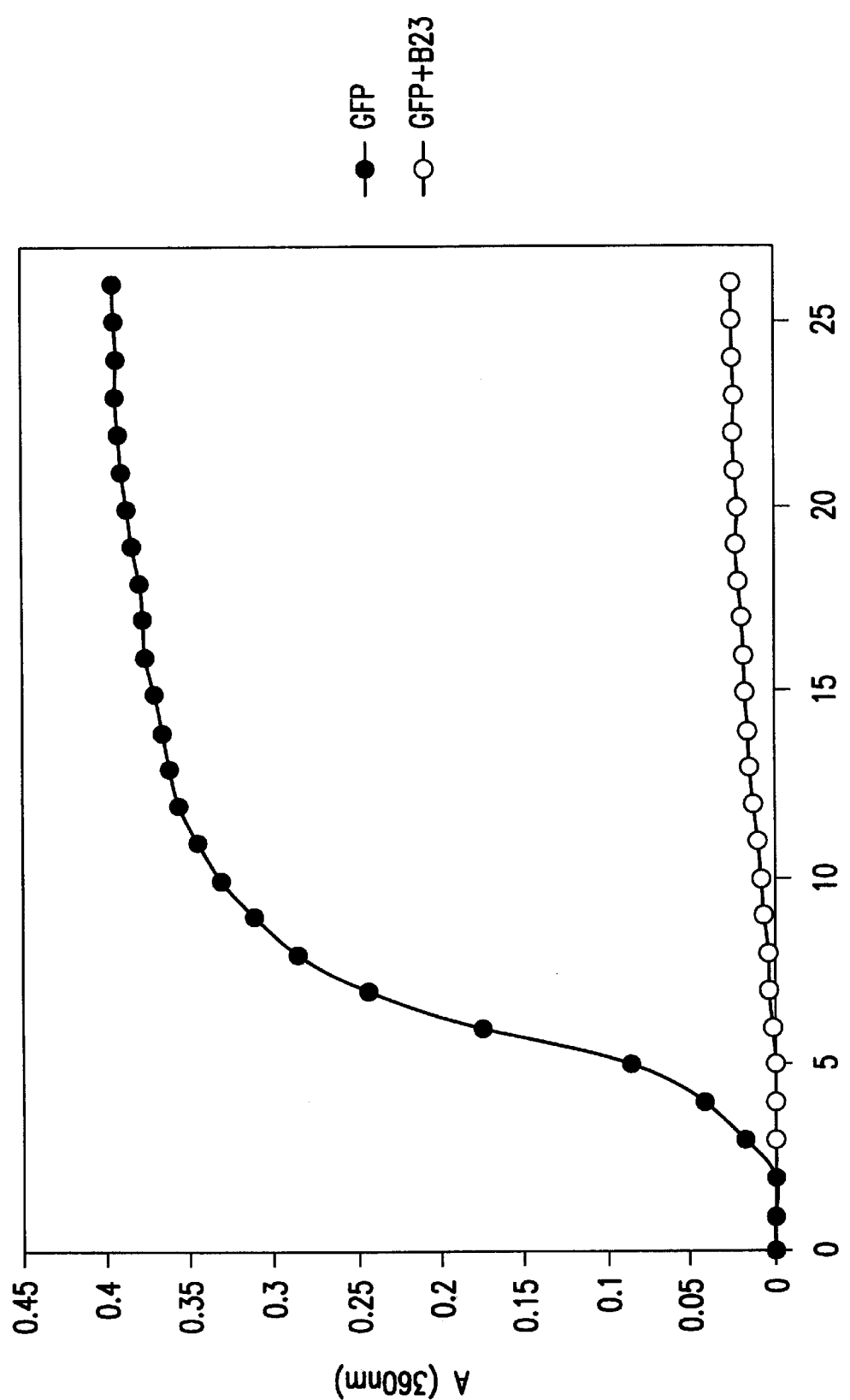

The effect of protein B23 on the thermal denaturation of green fluorescence protein at 75° C. is shown in FIG. 7B. The GFP protein was subjected to thermal denaturation in the absence or presence of an equimolar concentration of protein B23.

Figure 7C:
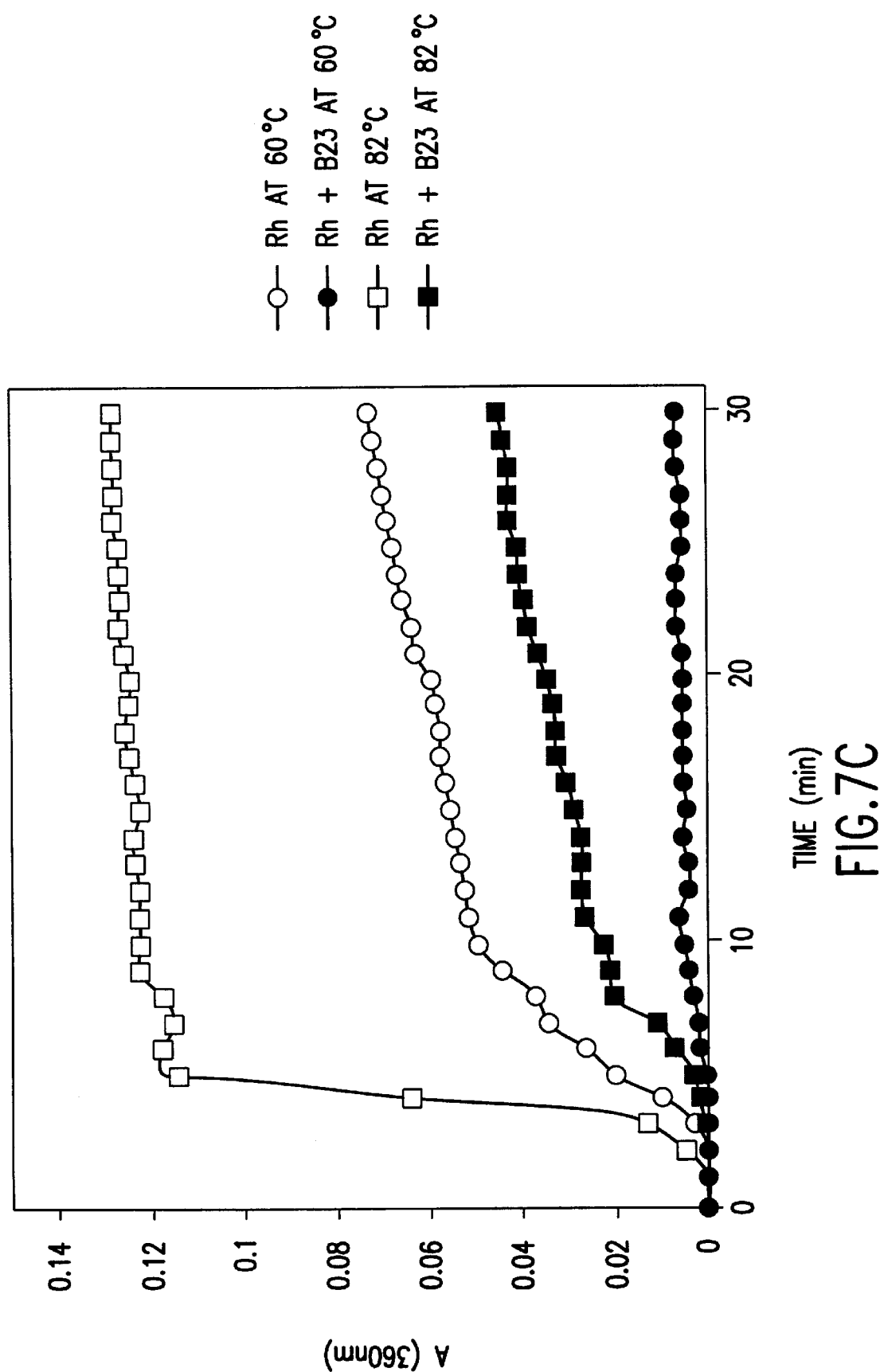

The effect of protein B23 on the thermal denaturation of rhodanese at 60 and 82° C. is shown in FIG. 7C.

Figure 7D:
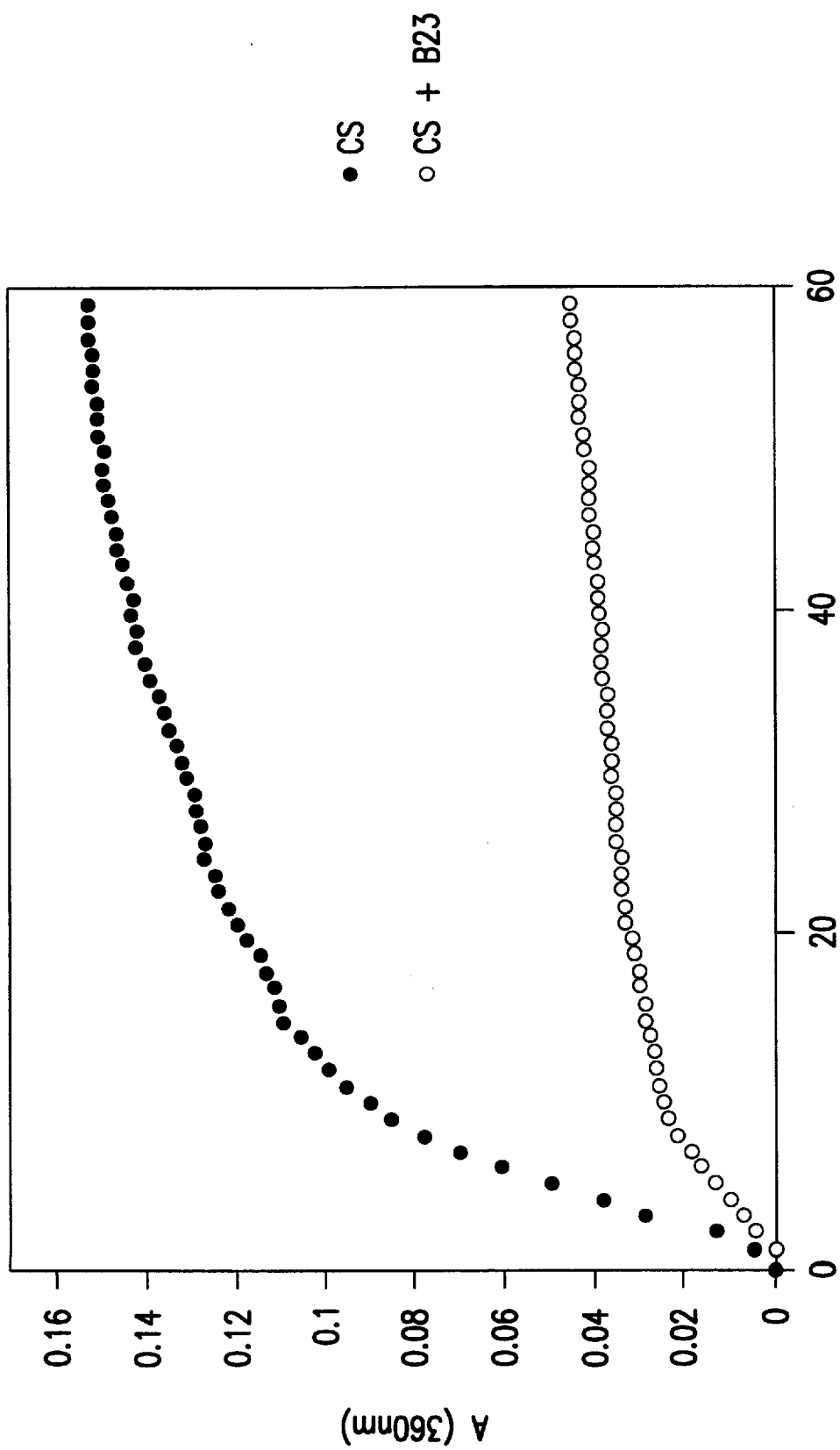

The effect of protein B23 on the thermal denaturation of citrate synthase at 65° C. is shown in FIG. 7D.

Figure 7E:
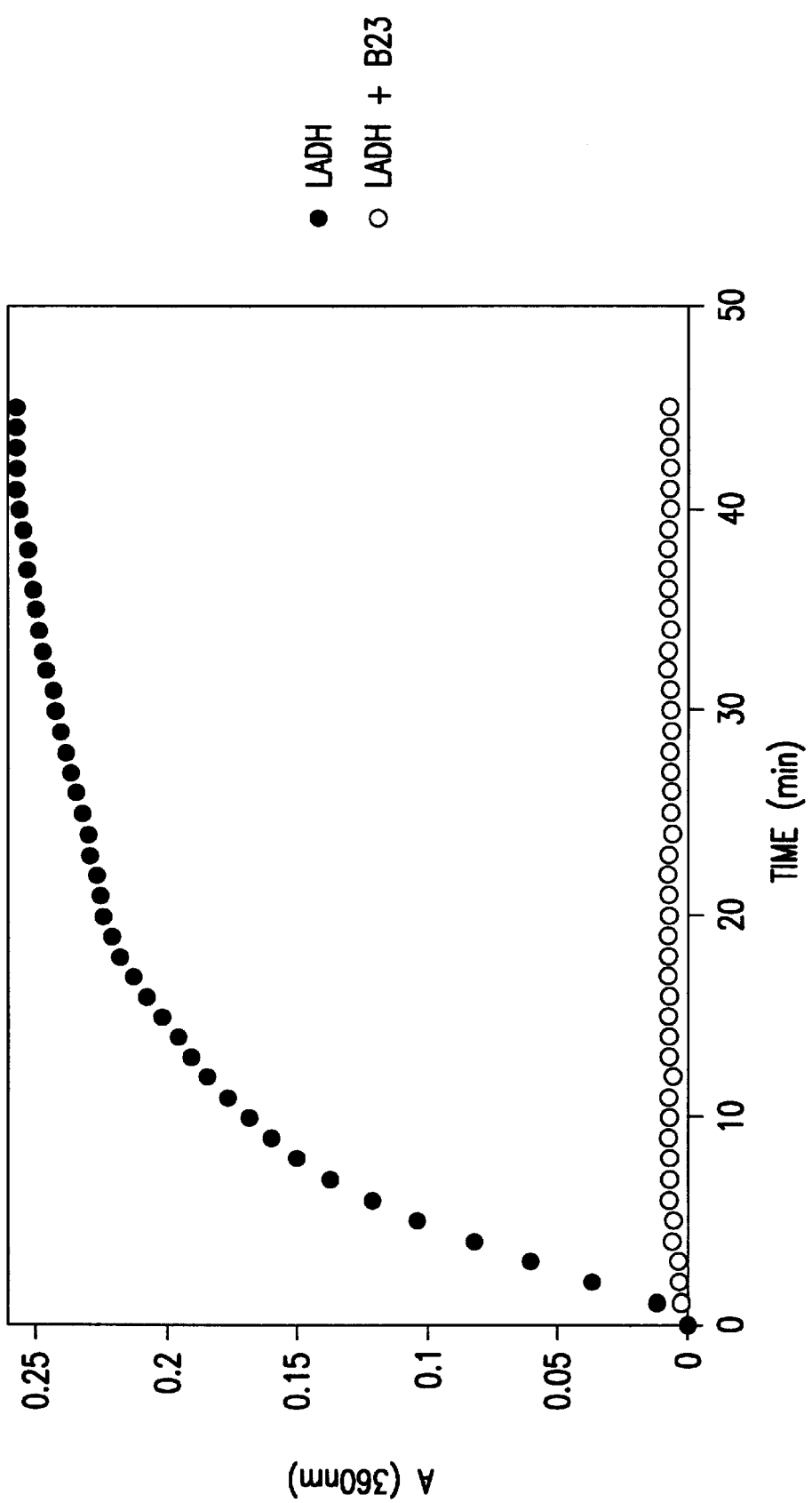

The effect of protein B23 on the thermal denaturation of liver alcohol dehydrogenase at 45° C. is shown in FIG. 7E.

These experiments indicate that protein B23 has molecular chaperone activity toward several enzymes (carbonic anhydrase, green fluorescent protein rhodanese, citrate synthase, and liver alcohol dehydrogenase) by preventing aggregation at elevated temperatures (up to 82° C.) when a 1:1 molar ration of protein B23 was added.

II. Protein B23 Preserves Enzyme Activities Under Conditions of Elevated Temperature Enzyme activity is a more sensitive measure of the native or denatured state of a protein than the aggregation assay. Therefore, enzyme activity measurements were done as a function of time under elevated temperature conditions.

Figure 8A:
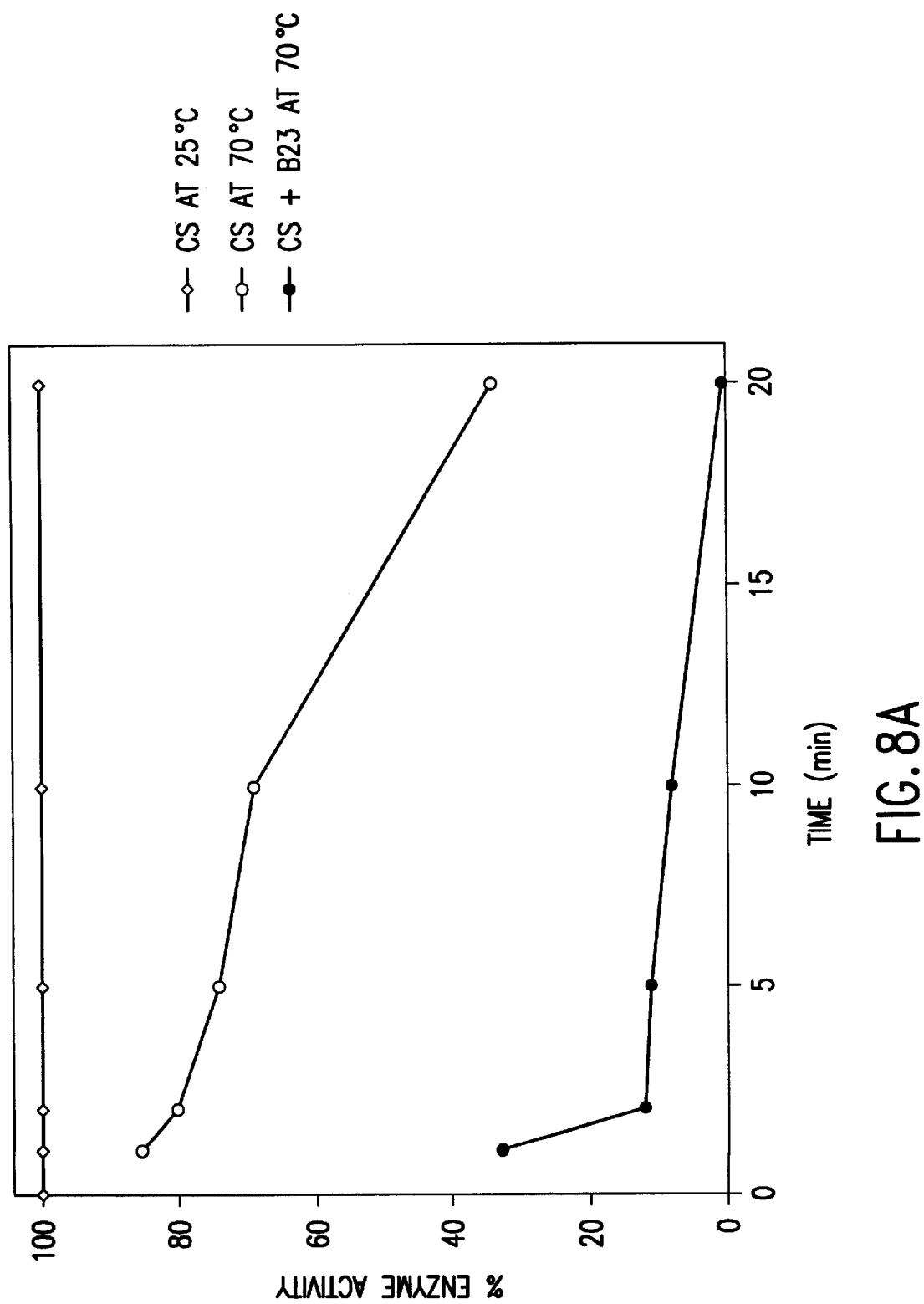
FIGS. 8A–8C are graphs showing the effect of protein B23 on the time course of thermal denaturation on various proteins.

Effect of protein B23 on the time course of thermal denaturation of LADH as measured by enzyme activity (FIG. 8A). LADH was incubated at 50° C. in the absence or presence of protein B23 at a molar ratio of 1:1 (B23:LADH). During heating, LADH lost enzyme activity very rapidly; i.e. within two minutes. However, when protein B23 was present the enzyme retained nearly complete activity. In control experiments it was found that the addition of B23 to an untreated solution of LADH did not influence the specific activity of the enzyme, nor did the presence of BSA protect the activity of LADH under the conditions used. Thus, protein B23 preserves the activity of LADH during thermal denaturation. Similar analyses were performed on two other enzymes, citrate synthase and rhodanese; the result were generally very similar to those obtained with LADH.

Figure 8B:
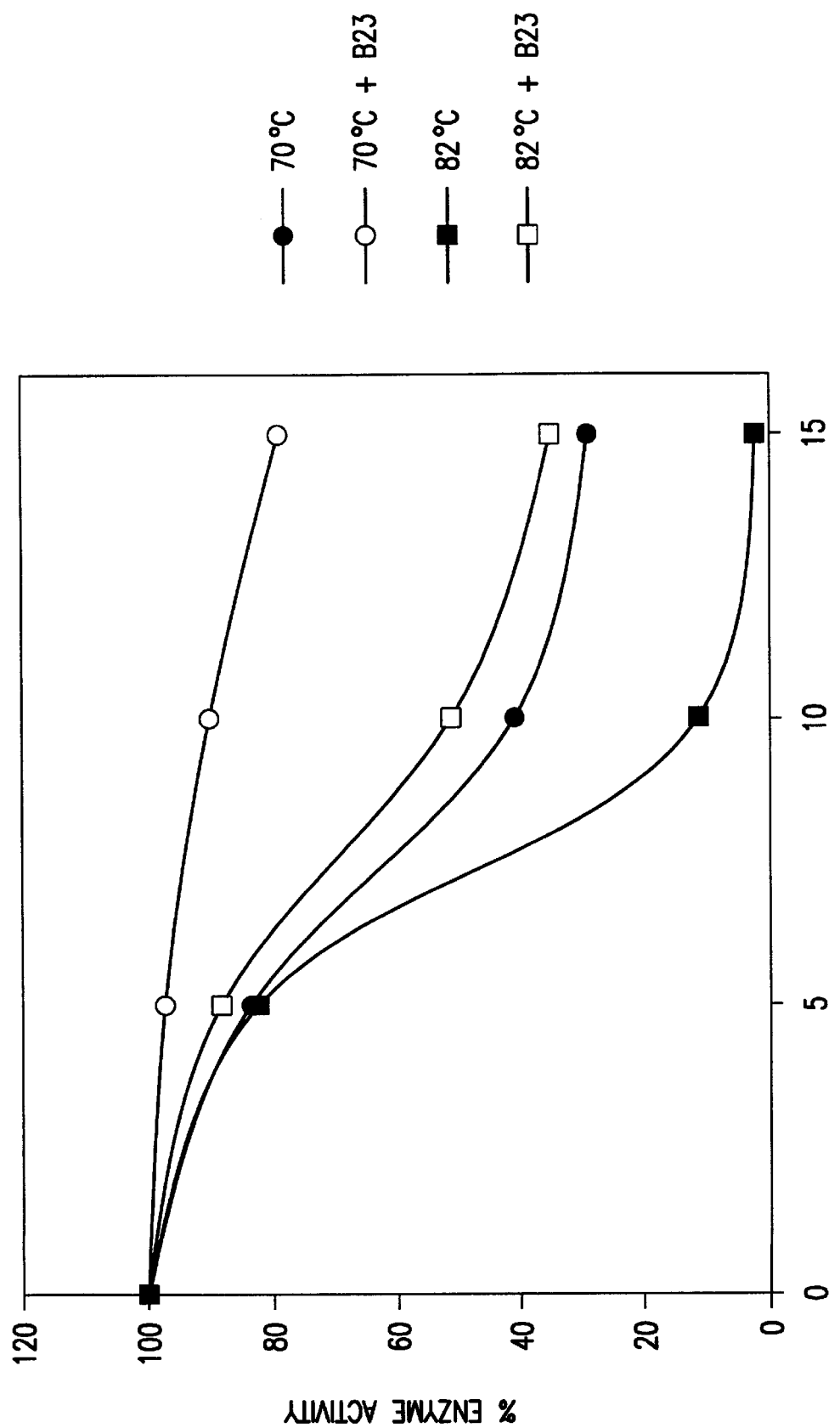
Figure 8C:
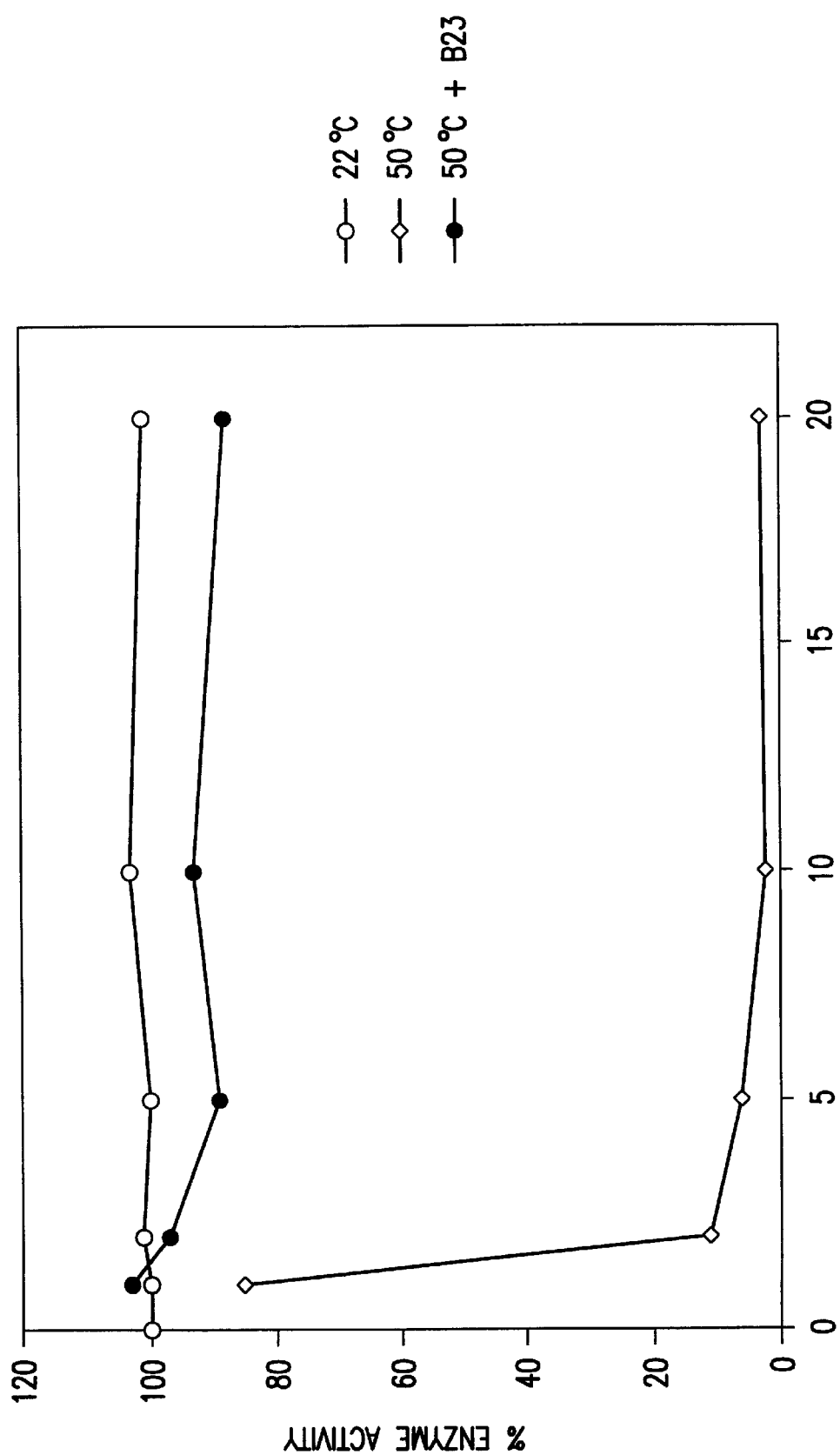

Effect of protein B23 on the time course of thermal denaturation of LADH and rhodanese as measured by enzyme activity. Similar results were obtained when citrate synthase was incubated at 70° C. (FIG. 8B) and rhodanese was incubated at two different temperature, 70° C. and 82° C. (FIG. 8C). Stoichiometric amounts of protein B23 were present during denaturation in both cases.

III. Protein B23 Increases the Long-term Stability of Enzymes

Figure 9A:
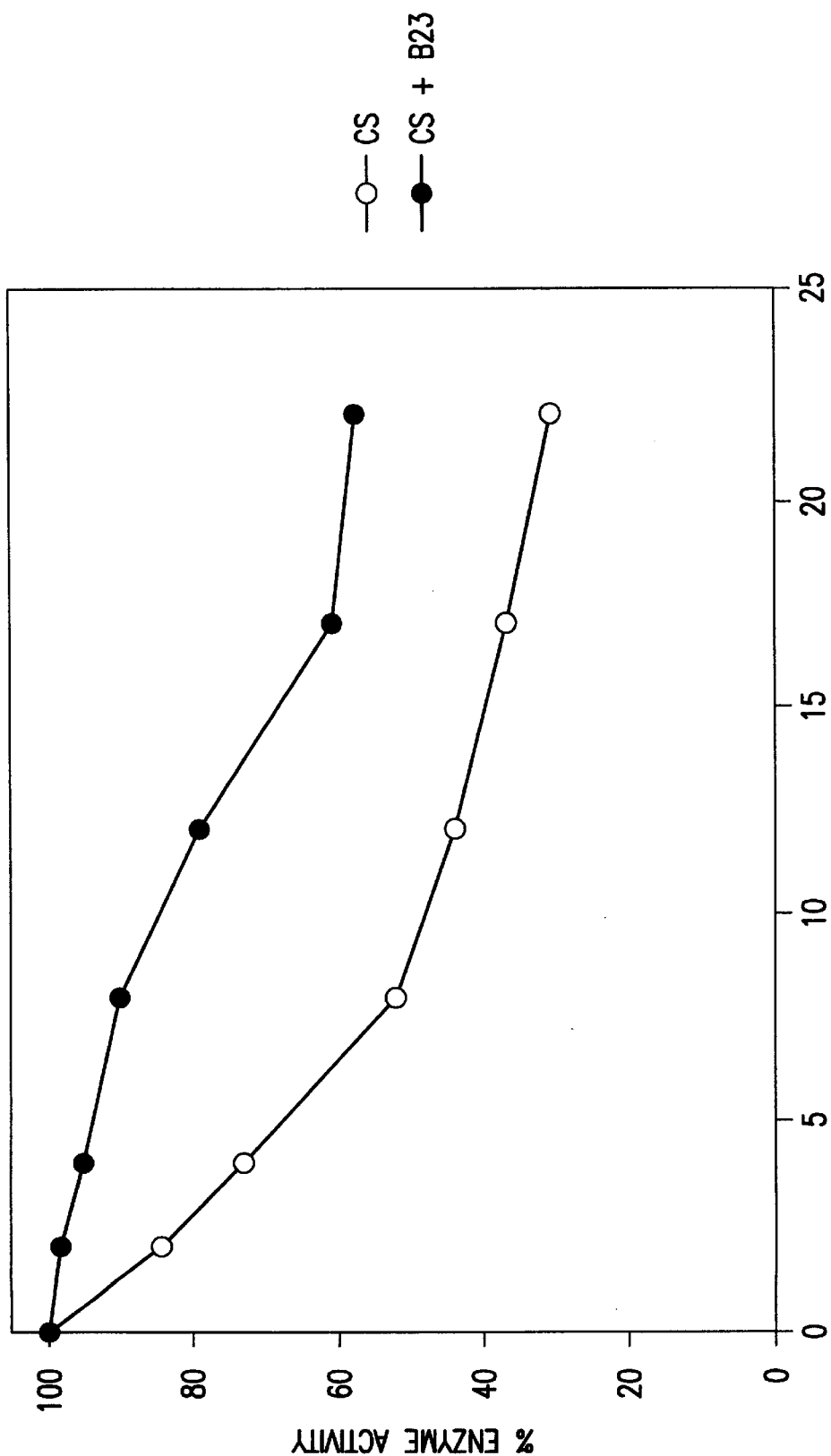
FIGS. 9A–9B are graphs showing the effect of protein B23 on the long-term stability of various proteins.

Effect of protein B23 on the long-term stability of liver alcohol dehydrogenase in solution at room temperature—LADH (1 mg/ml) was dissolved in 50 mM Tris buffer (pH 7.6), which included 0.02% sodium azide and stored at room temperature for up to 23 weeks in the absence or presence of equimolar concentrations of protein B23. The enzyme activities were measured as described above at the times shown in FIG. 9A. These results indicate that protein B23 is capable of helping to prevent loss of enzyme activity of LADH when it is stored in solution at room temperature over long periods of time.

Figure 9B:
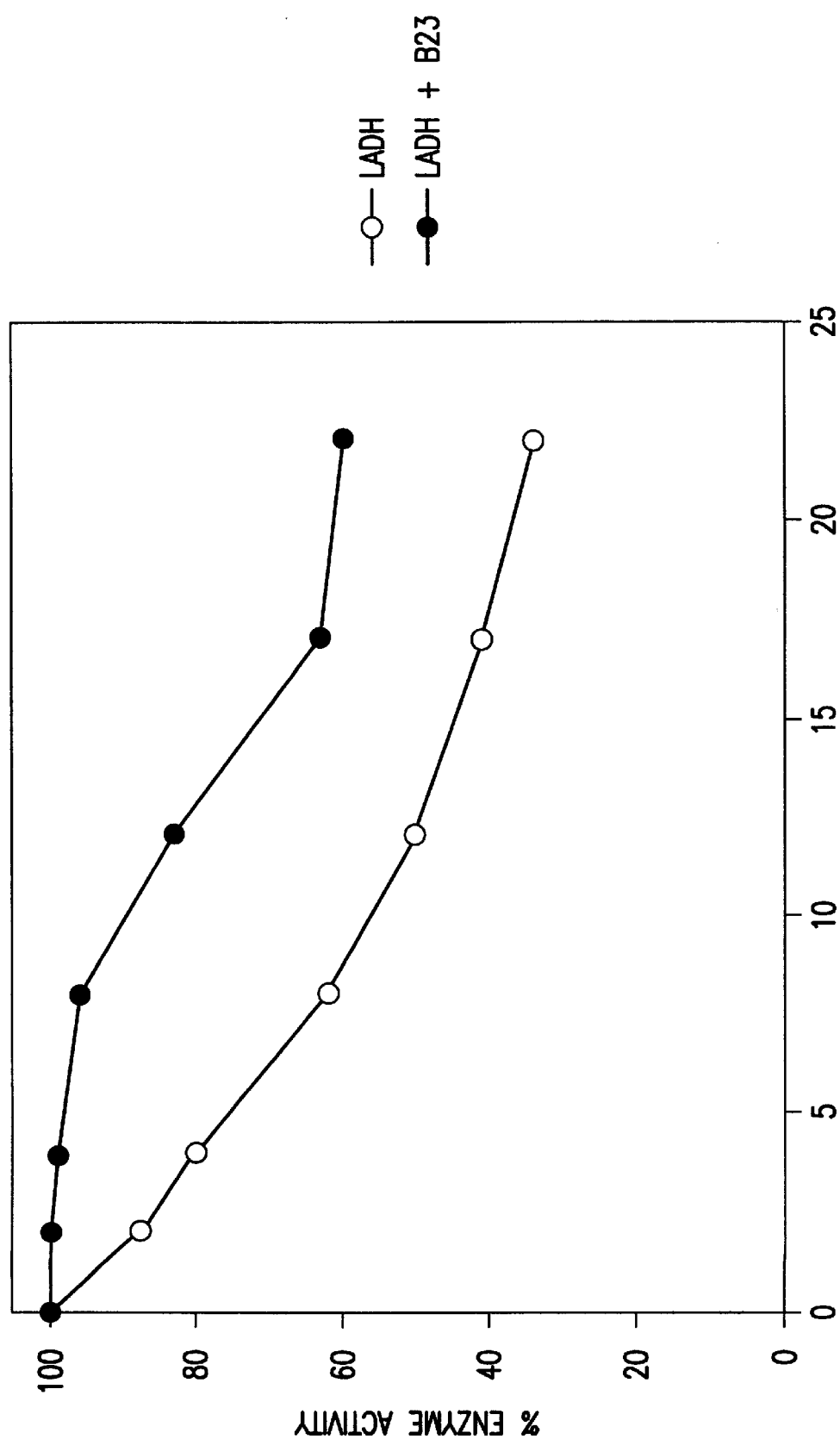

Effect of protein B23 on the long-term stability of citrate synthase in solution at room temperature—Similar results were obtained when citrate synthase was stored for up to 23 weeks. Citrate synthase (0.8 mg/ml) was dissolved in 50 mM Tris buffer (pH 7.8), which included 0.02% sodium azide and stored at room temperature for up to 23 weeks in the absence or presence of equimolar concentrations of protein B23. The enzyme activities were measured as described above at the times shown in FIG. 9B. These results indicate that protein B23 could increase the long term shelf life of citrate synthase or other enzymes kept in solution at room temperature.

IV. Protein B23 Promotes the Renaturation of Chemically Denatured Proteins

Many molecular chaperones not only protect proteins against the effects of denaturation, but they are also capable of promoting the refolding of denatured proteins. Two substrates, LADH and rhodanese were used for testing this activity in protein B23.

Figure 10A:
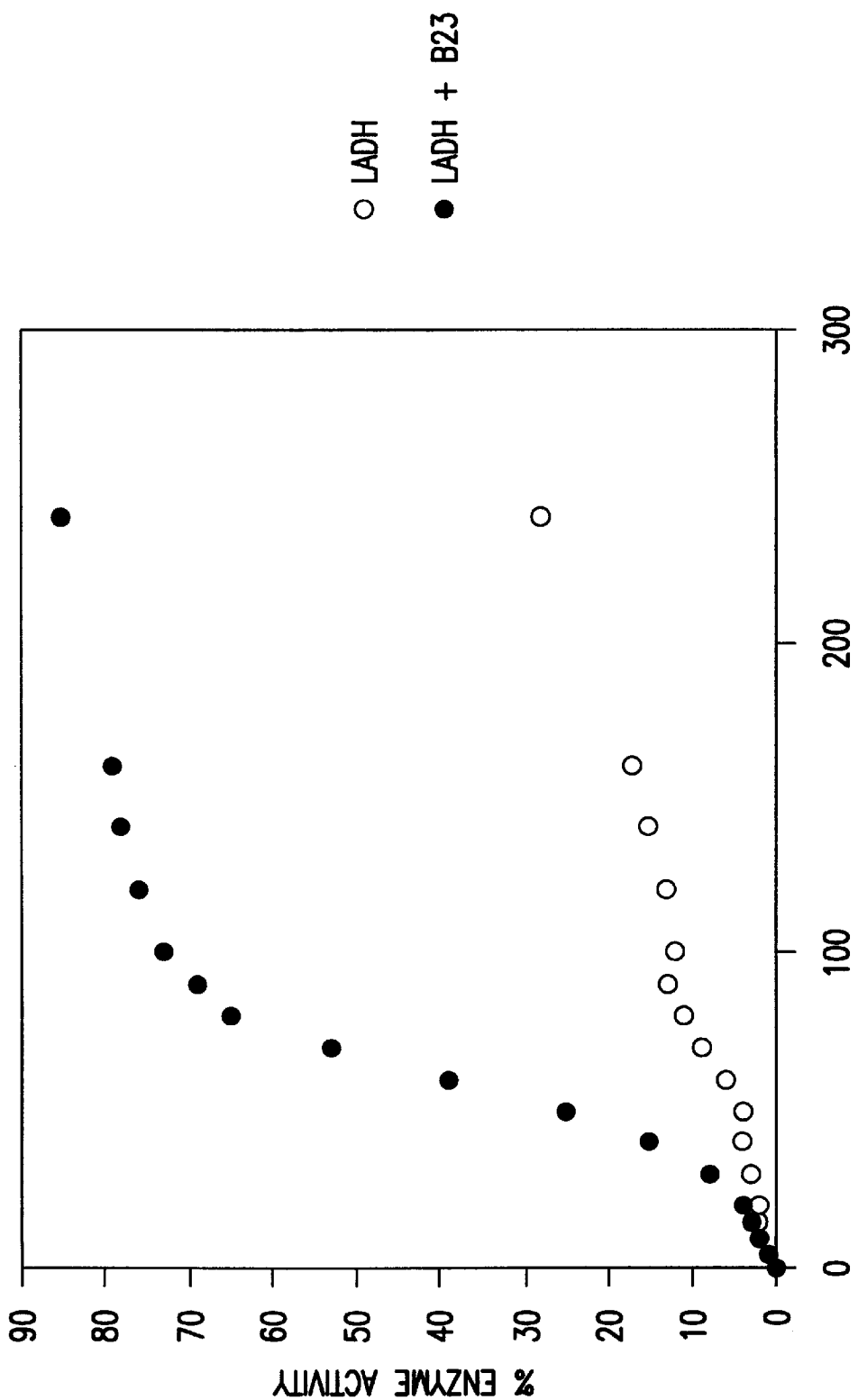
FIGS. 10A–10B are graphs showing the effect of protein B23 on the reactivation kinetics of various proteins.

Protein B23 promotes the renaturation of chemically denatured LADH—LADH was denatured in 6 M guanidine hydrochloride and diluted 100-fold as above. The catalytic activity of the enzyme was measured after refolding in the absence or presence of protein B23 at a molar ratio of 1:1 (B23:LADH). FIG. 10A shows the time course of reactivation of LADH by protein B23. The enzyme was completely inactive after denaturation and dilution although there was a very slow restoration of the activity after several hours at room temperature. However, when B23 was present, 76% of the original activity was regained after 3 hours. In control experiments it was found that the addition of B23 to a native solution of LADH did not influence the specific activity of the enzyme. Furthermore, addition of BSA to the renaturing solution did not accelerate the recovery of enzyme activity.

Figure 10B:
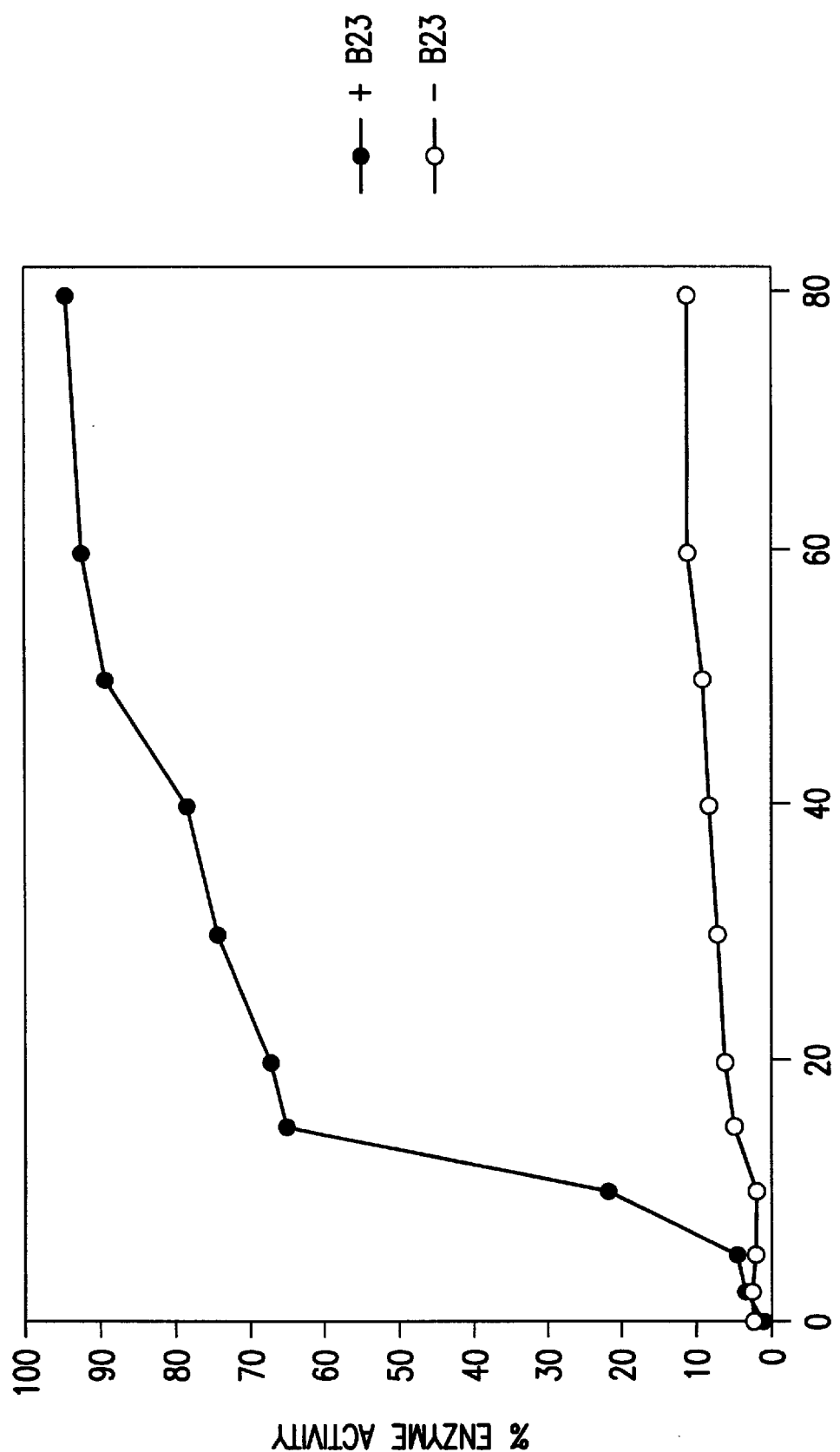

Protein B23 promotes the renaturation of chemically denatured rhodanese—Similar results were obtained when rhodanese was used as a substrate for renaturation (FIG. 10B). Rhodanese was denatured in 6 M guanidine hydrochloride and diluted 100-fold as described in the METHODS AND REAGENTS section (Yoshida 1998). In this case only about 10% of the original activity was regained 80 minutes after dilution of the guanidine HCl in the absence of protein B23. However, the enzyme recovered more than 95% of its activity when incubated with an equimolar quantity of protein B23 for 80 min at room temperature. Thus, protein B23 not only prevents aggregation and protects catalytic activity but it is also able to promote the renaturation of denatured proteins.

V. The Presence of Protein B23 Increases the Temperature Optimum of an Enzyme

Figure 11:
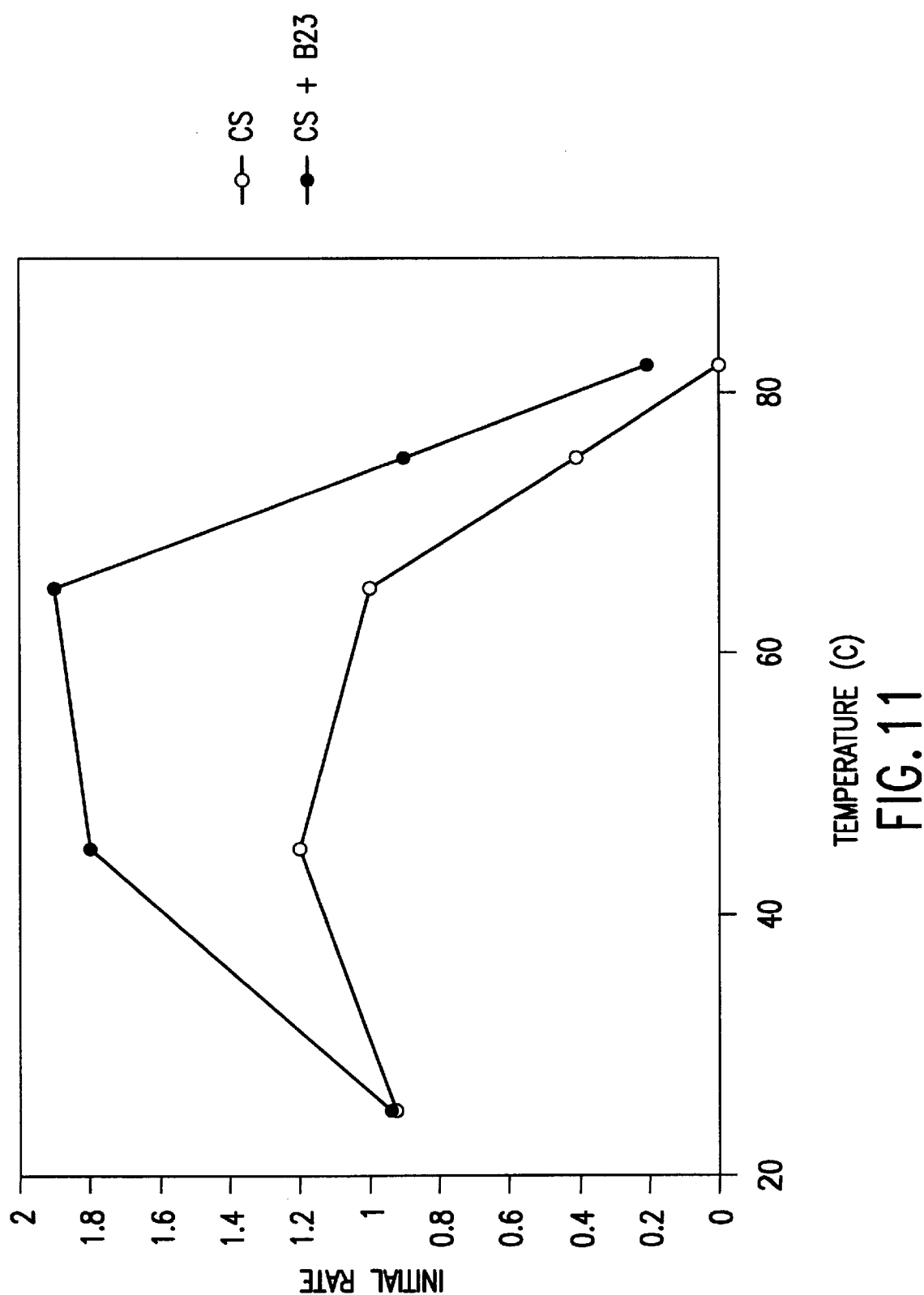
FIG. 11 shows the effect of protein B23 on the temperature optimum for the activity of citrate synthase.

Effects of protein B23 on the temperature optimum of citrate synthase—The initial rate of enzyme activity of citrate synthase was monitored at different temperatures in the absence and presence of protein B23 as described above. As FIG. 11A shows, the temperature optimum of citrate synthase is approximately 45° C. In the presence of B23 this optimum shifted to about 65° C., and the initial rate of citrate synthase was also increased. These data suggest that protein B23 is not only capable of increasing the stability of the enzyme, but also increasing the temperature optimum. This property could be used to accelerate the rate at which enzymes catalyze reactions in certain applications.

VI. Protein B23 Expression Induces Thermotolerance in Bacteria

Figure 12:
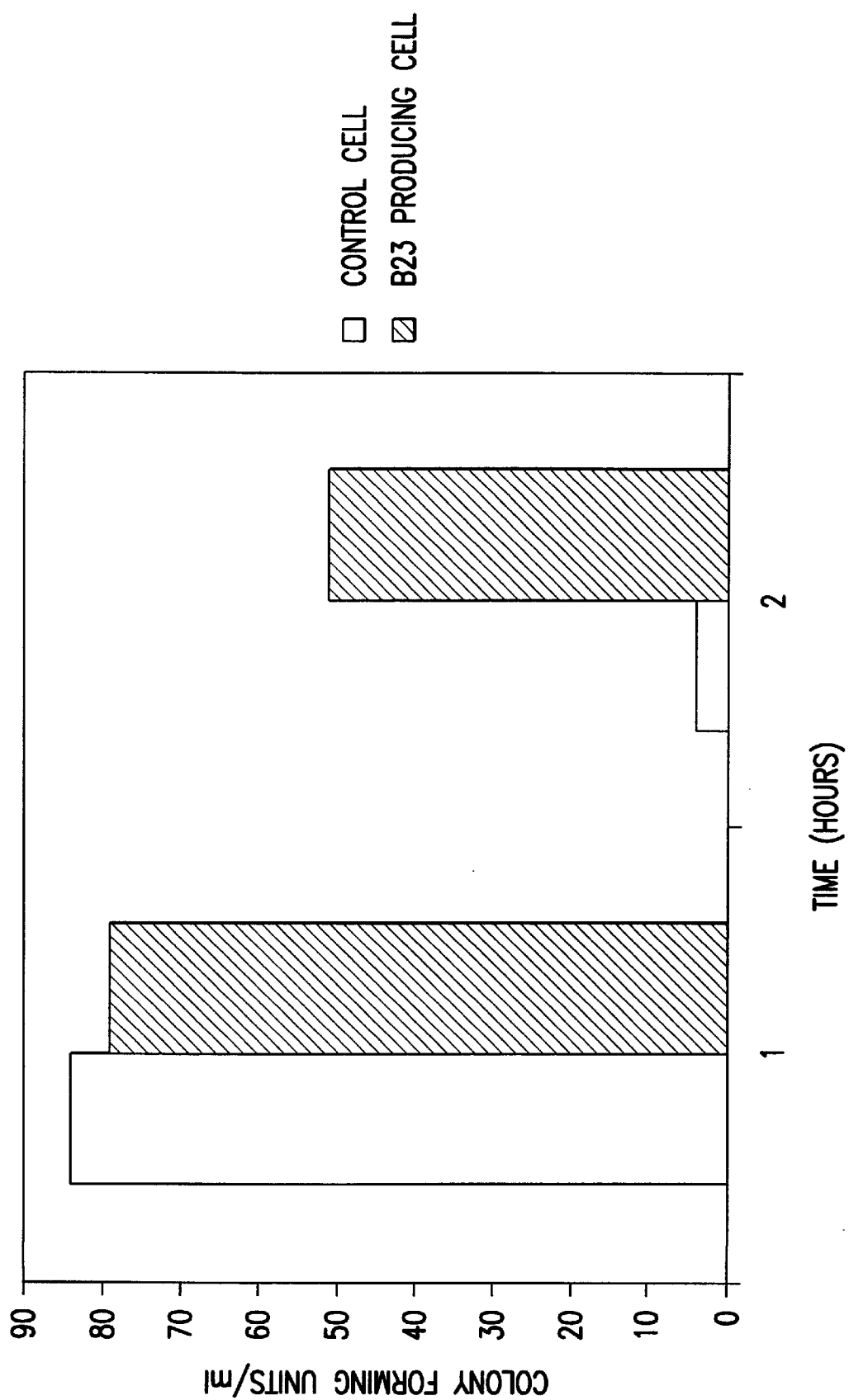
FIG. 12 shows that E. coli cells expressing protein B23 are protected from the effects of elevated temperatures (at 50° C.) after 12 hours.

E. coli cells expressing protein B23 are protected from the effects of elevated temperatures—To determine whether B23 can confer heat resistance in vivo, E. coli cells expressing the protein from the B23 cDNA inserted into the pET11c vector were divided into two sets of cultures containing equal numbers of cells. Both sets were incubated at 37° C. for 30 min, but only one of them in the presence of IPTG to induce production of B23. Both were then incubated at 50° C. for various times and the number of surviving cells was determined by plating aliquots on Luria plates and counting colonies. After 12 hours at 50° C. survival was minimal in the uninduced cells but was greater than 60% in the cells expressing protein B23 (FIG. 12). This experiment shows that protein B23 can have a protective effect against the destructive effects of high temperatures on living cells.

Figure 13A:
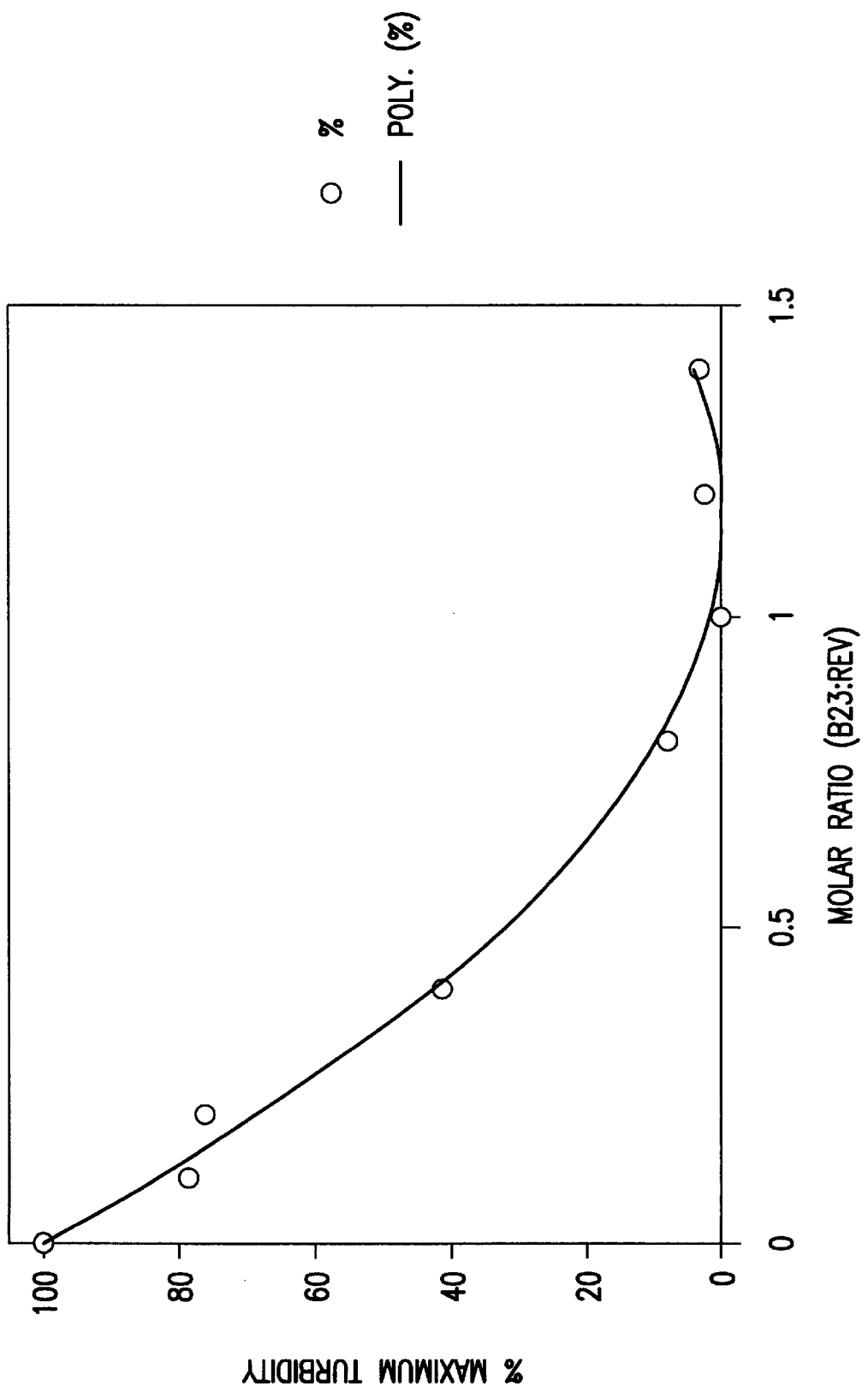
FIGS. 13A–13B are graphs showing the effect of protein B23 on temperature-independent aggregation of various proteins.

VII. The Presence of Protein B23 Prevents Temperature-independent Aggregation of Other Proteins Effect of protein B23 on the temperature-independent aggregation of the HIV-1 Rev protein—Aliquots of Rev protein solution (0.5 mg/ml in 50 mM sodium phosphate buffer, pH 7.0, containing 150 mM NaCl, 200 mM KCl and 1 mM DTT) were dialyzed against 20 mM sodium phosphate buffer (pH 7.0) containing 1 mM DTT at 4 C. The samples included increasing amount of protein B23 as indicated by the ratios of Rev:B23 (FIG. 13A). The turbidity was measured at 360 nm after overnight dialysis. Data are expressed as the percentage of the maximum turbidity. The samples containing Rev alone showed the greatest level of turbidity, whereas addition of increasing concentrations of protein B23 resulted in decreasing As with the temperature-dependent aggregation described above the solutions were essentially clear when the B23:Rev ratio was greater than one. Thus, the ability of protein B23 to inhibit Rev aggregation can be seen under several different conditions of ionic strengths and temperature.

Figure 13B:
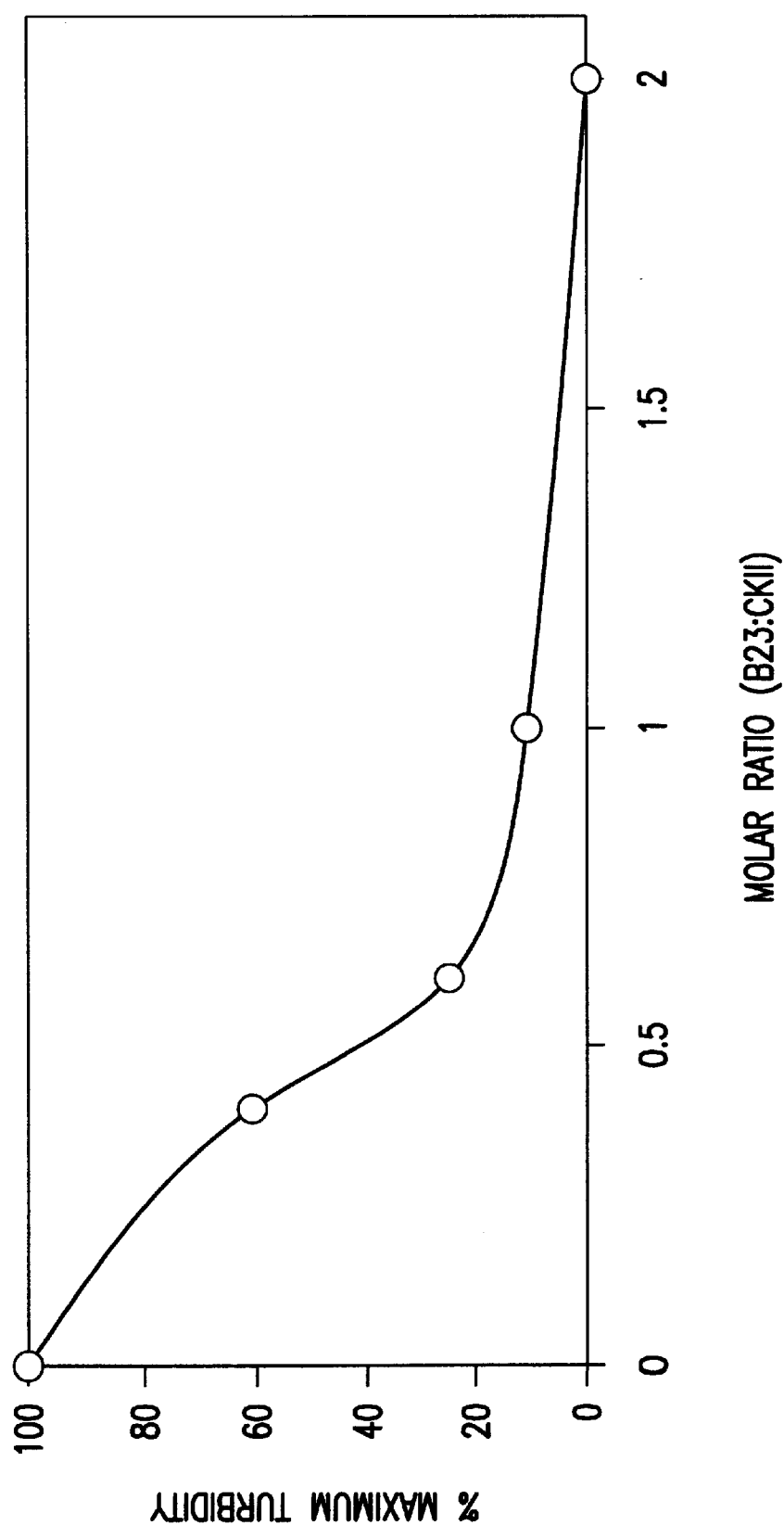

Effect of protein B23 on aggregation of CKII at low ionic strength—Aliquots of CKII solution (0.11 mg/ml in 50 mM Tris-HCl pH 7.8, containing 250 mM NaCl, 1 mM DTE and 0.1 mM PMSF) were dialyzed against 25 mM Tris-HCl pH 7.8 (pH 7.8) containing 1 mM DTE at 4 C. The samples included increasing amount of protein B23 as indicated by the ratios of CKII:B23 (FIG. 13B). The turbidity was measured at 360 nm after overnight dialysis. Data are expressed as the percentage of the maximum turbidity.

Figure 14A:
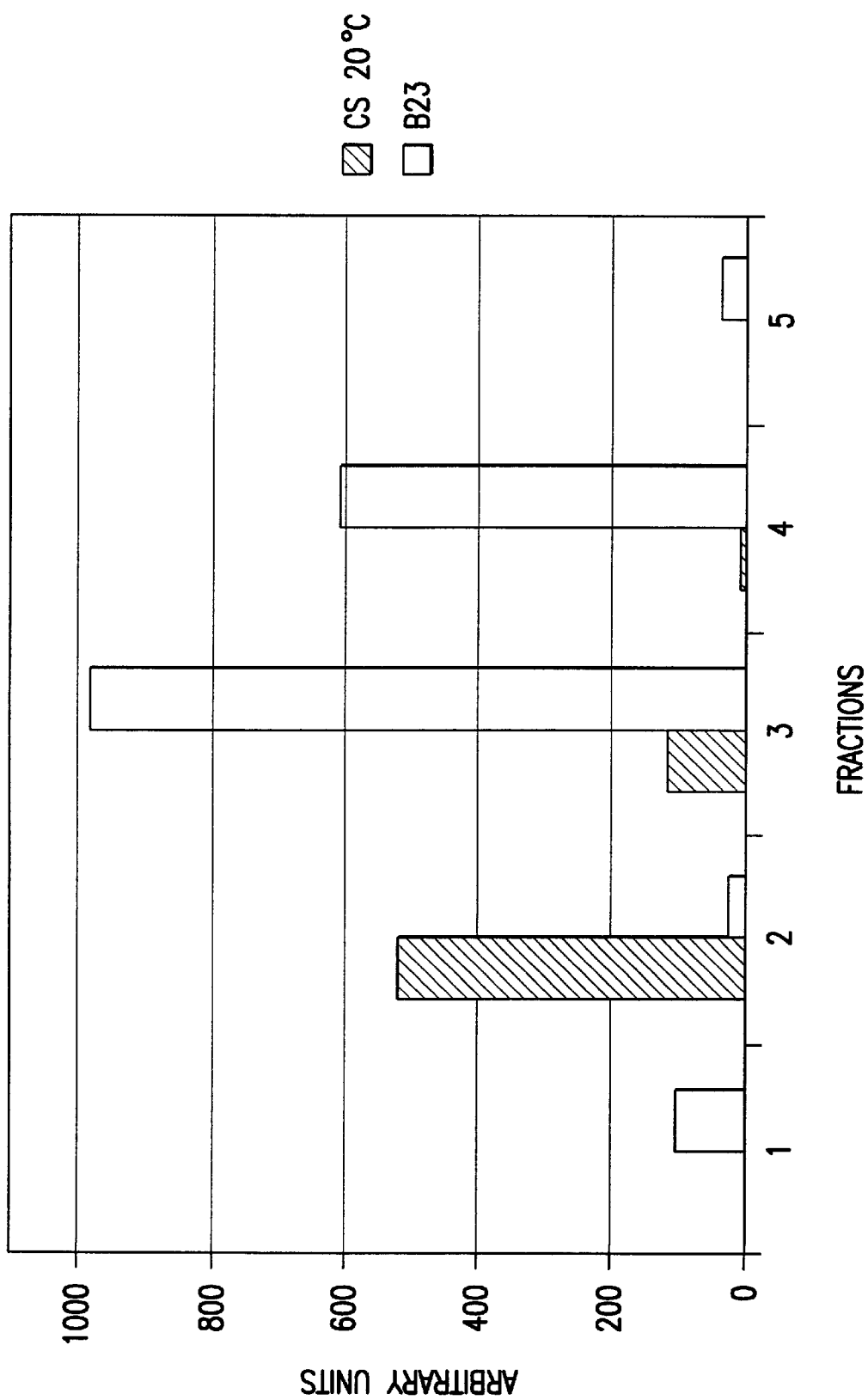
FIGS. 14A–C are graphs showing the effect of phosphorylation of protein B23 by CKII on the release of citrate synthase from the B23-citrate synthase complex as analyzed by sucrose density gradient sedimentation.
Figure 14B:
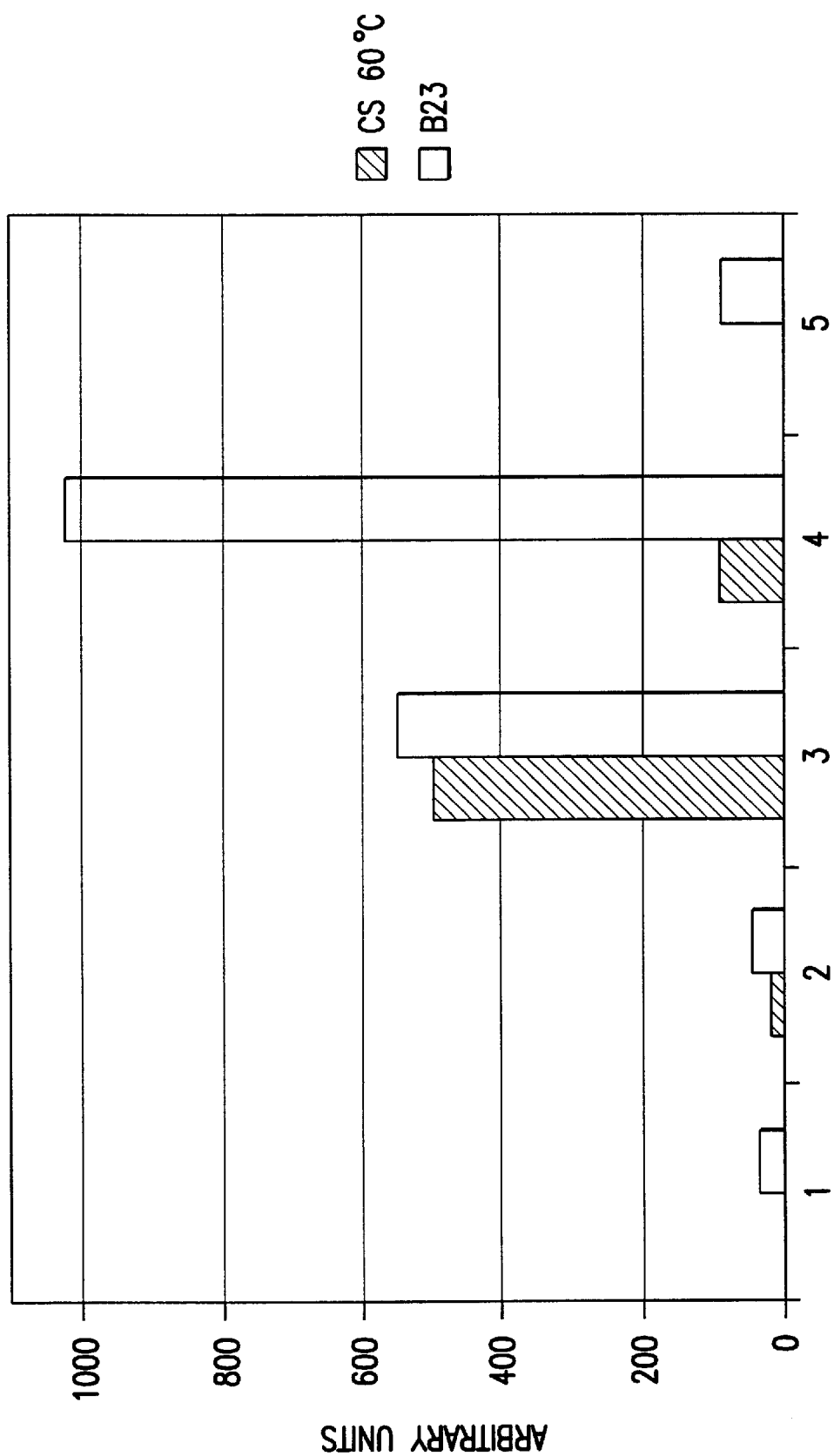
Figure 14C:
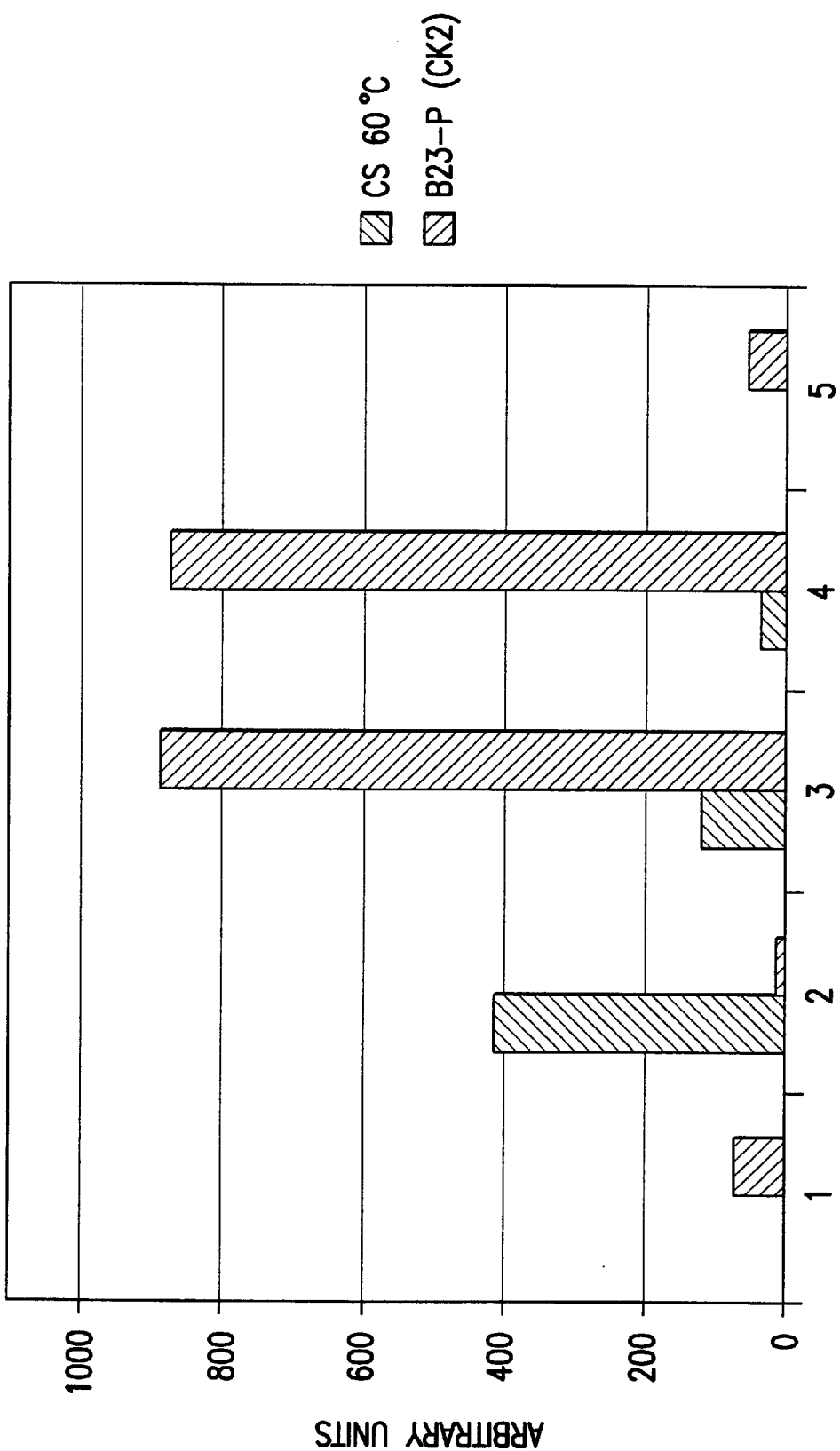

VIII. Phosphorylation of Protein B23 by Casein Kinase II Permits Release of the Bound Protein Substrate Effect of CKII phosphorylation of protein B23 on release of chaperone substrates—Equimolar mixtures of $^{125}$I-labeled protein B23 and citrate synthase were subjected to various treatments and analyzed by sucrose density gradient sedimentation (FIGS. 14A–C). The samples were layered onto 5–30% sucrose gradients in 50 mM tris-HCl buffer (pH 7.8) and centrifuged in a Beckman 100.3 rotor for 120 min at 100,000 RPM. Fractions (0.5 ml) were collected and the radioactivity of protein B23 and the enzyme activity of citrate synthase were measured as described by Buchner et al. (1998). When the untreated proteins were analyzed as such they sedimented as separate peaks, indicating that they did not interact with each other (FIG. 14A). However, when the mixture of the two proteins was treated at 65° C. for 30 min prior to loading on the centrifuge gradient, a substantial amount of both proteins sedimented together in fraction 3 (FIG. 14B). This suggests that protein B23 preferentially binds denatured proteins. When the heat-treated complex was phosphorylated by CKII and then subjected to sedimentation analysis, the two proteins again sedimented as separate peaks (FIG. 14C). This indicates that phosphorylation of protein B23 allows it to release its bound substrate.

Figure 15A:
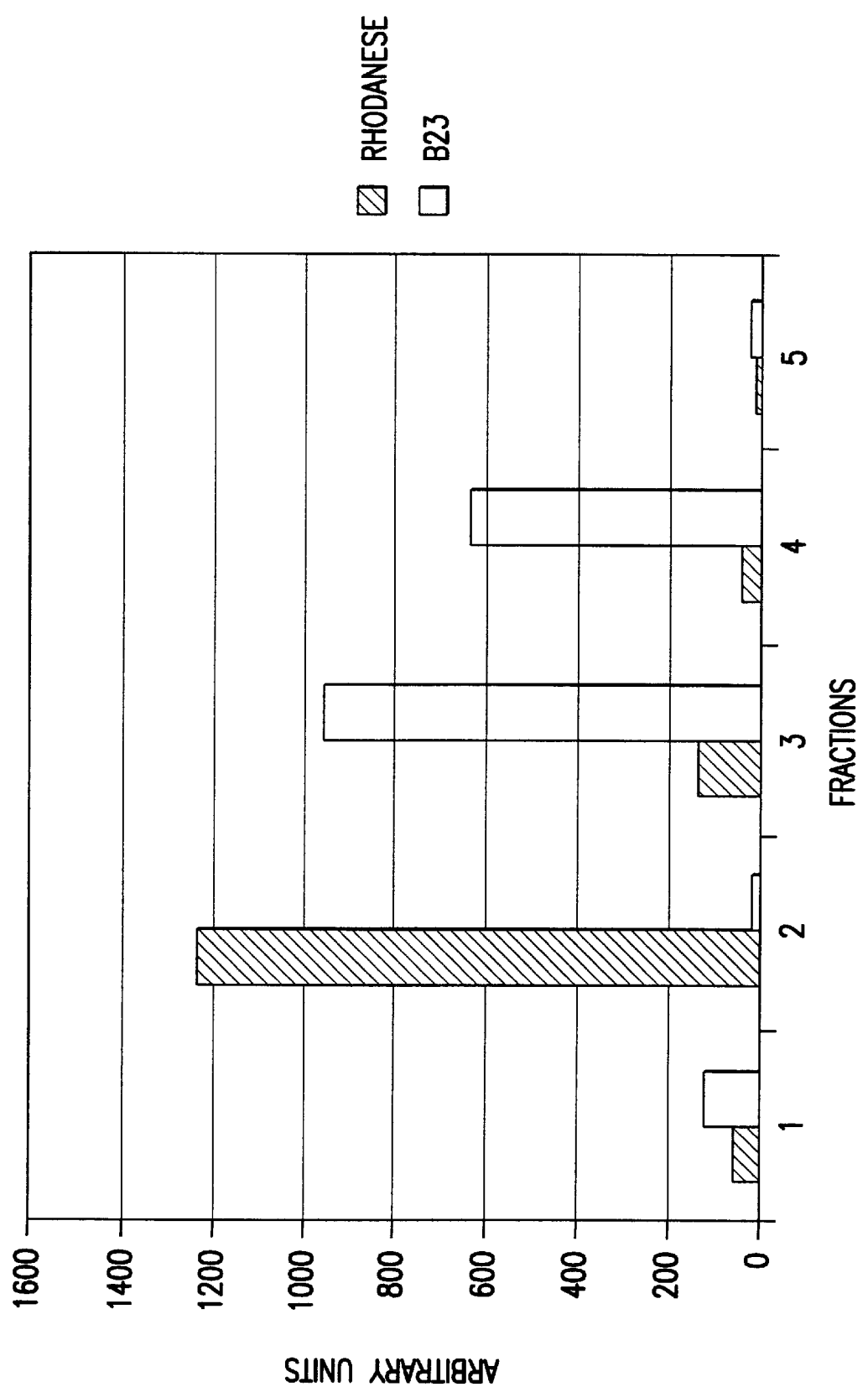
FIGS. 15A–C are graphs showing shows the effect of CKII phosphorylation of protein B23 on the release of rhodanese from the B23-rhodanese complex as analyzed by sucrose density gradient sedimentation.
Figure 15B:
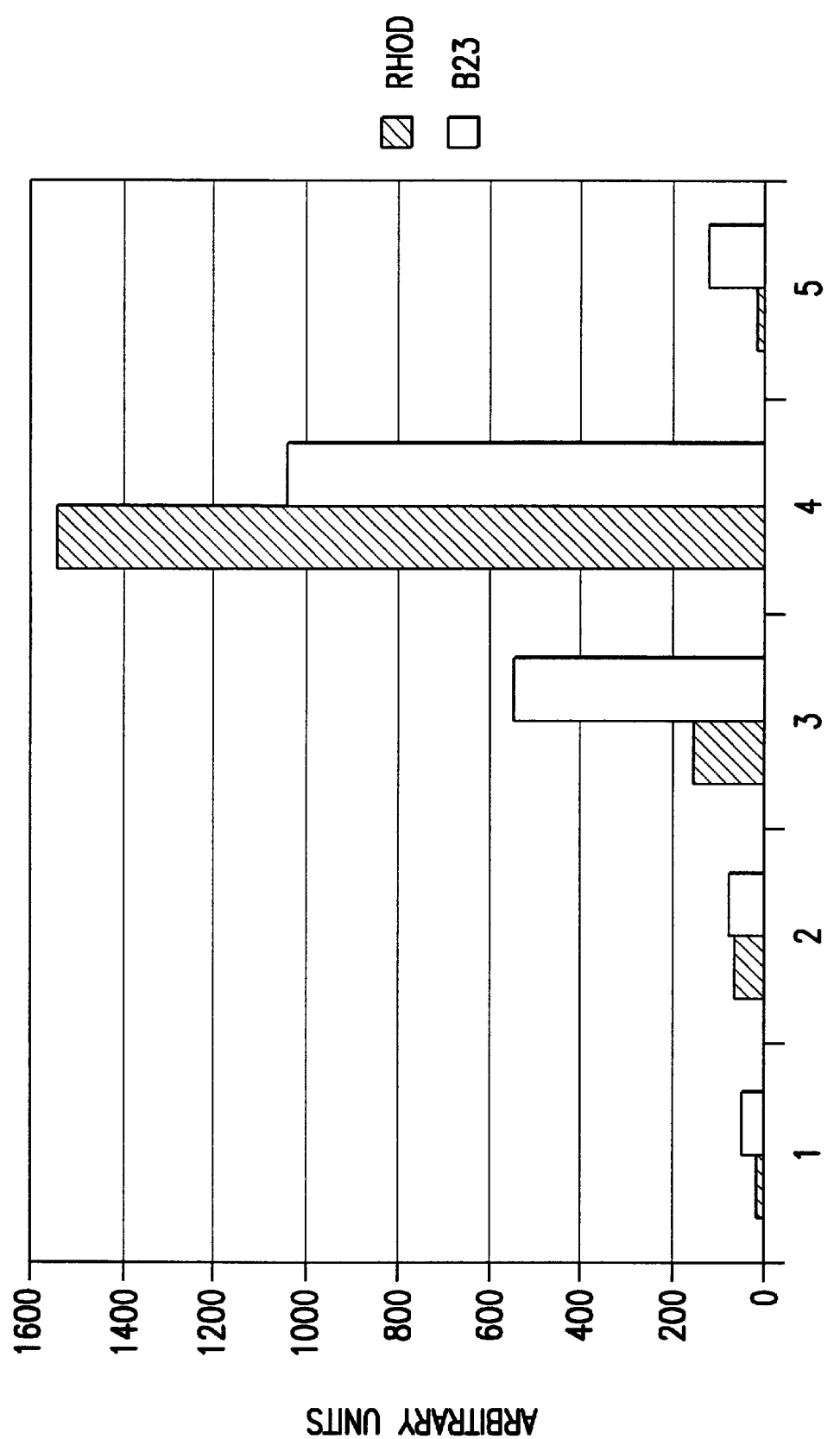
Figure 15C:
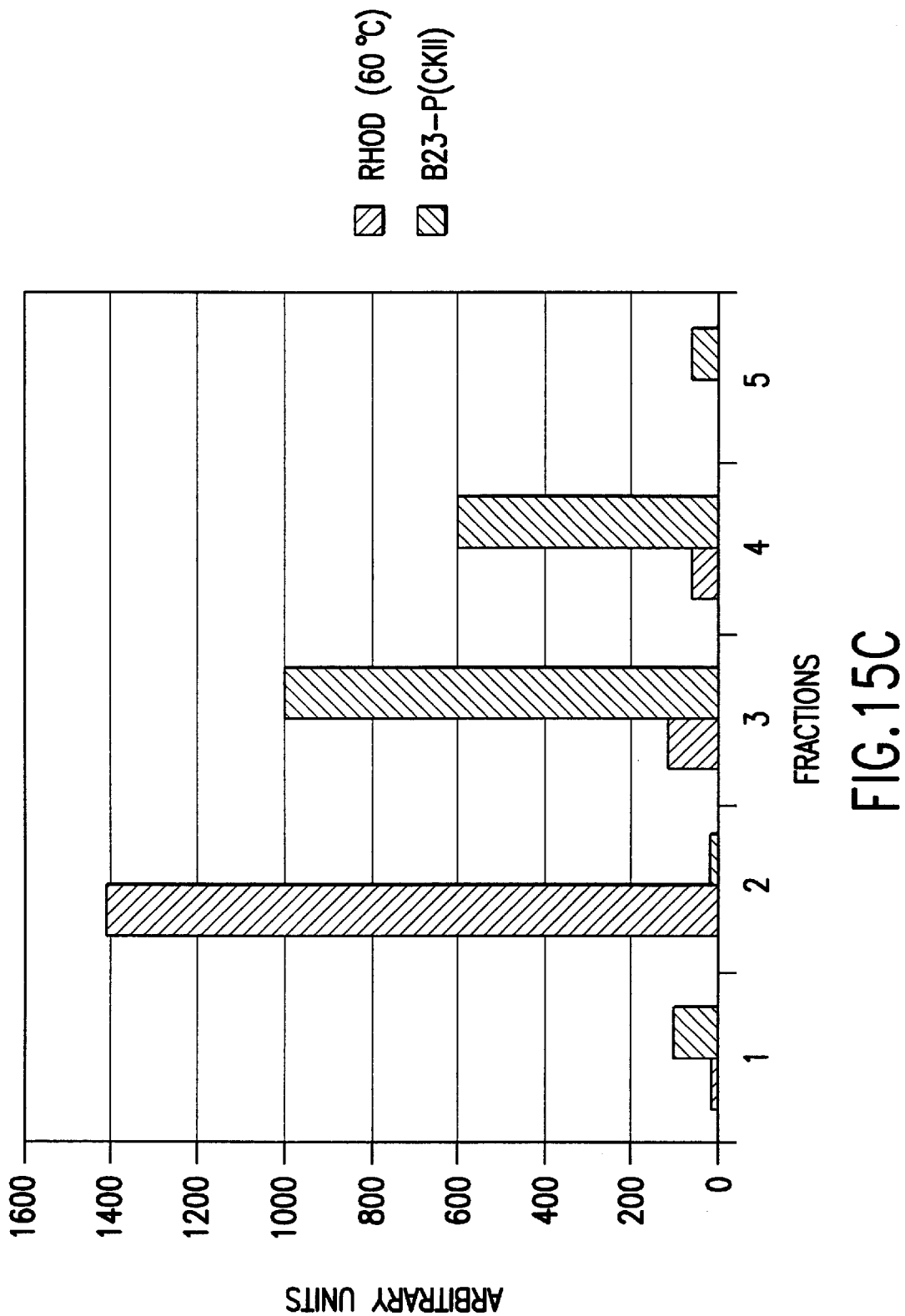

Similar results were obtained when $^{125}$I-labeled CKII phosphorylated and unphosphorylated protein B23-rhodanese complexes were analyzed under conditions similar to those used for the experiments with citrate synthase (FIG. 15A–C). Rhodanese (250 µg/ml) was incubated with an equimolar concentration of labeled protein B23 at room temperature or at 65° C. for 30 min in 50 mM tris-HCl buffer (pH 7.8). The samples were analyzed by sucrose density gradient sedimentation as above. As with citrate synthase, in the untreated sample, protein B23 and rhodanese sedimented separately (FIG. 15A). Rhodanese activity was measured essentially as described by Taguchi and Yoshida (1998). In the heated sample, the two proteins cosedimented in the same fraction, indicating that a complex was formed (FIG. 15B). However, when the denatured complex was treated with CKII, the two proteins again were found in separate fractions in the sucrose gradient. This shows that phosphorylation of protein B23 in a complex causes the release of bound substrate proteins.

The above studies provide a means of releasing bound proteins from protein B23. Thus, when protein B23 is used to recover denatured target proteins, the production of purified target protein will be simplified by releasing the bound target protein from B23.

EXAMPLE III

Co-expression of protein B23 with another recombinant protein in E. coli.—B23 may be co-expressed with a protein of interest by two different methods: 1) expression of the two different mRNAs from separate plasmids and 2) expression as a bicistronic message from a single plasmid. Method 1 has been used previously for co-expression of two different proteins for at least two different applications. (Maier et al., 1999; Cole, 1996.)

Expression from two separate plasmids—The Qiagen system may be used for co-expression of B23 and a protein of interest. In this system, the cDNA for the protein of interest is be placed in one of the pQE expression plasmid vectors and the protein B23 cDNA is inserted into the regulatory plasmid pREP4. The pREP4 plasmid contains the p15A replicon, which is compatible with the ColE1 origin of replication in the pQE vectors. Although the expression system is commercially available from Qiagen, the pREP4 plasmid is not. Plasmid pREP4 may be prepared from E. coli host strains (either M15[pREP4] or SG13009[pREP4]), both available from Qiagen. The pREP4 plasmid is prepared from a culture of either E. coli host strain by the alkaline lysis method (Birnboim, 1983). The pREP4 plasmid is digested with restriction endonuclease XbaI and the resulting linearized plasmid will be isolated in preparation for insertion of the B23 cDNA. Because the pREP4 plasmid is not engineered for the general expression of recombinant proteins, it is necessary to insert the B23 cDNA along with a ribosome binding site and promoter compatible with the expression system. This can be achieved by utilizing the latter two elements from the pQE vectors.

Initially, the protein B23 cDNA is inserted into the pQE-30 vector commercially available from Qiagen. This construct is then be subjected to PCR using primers that amplify the sequence containing the promotor, the ribosome binding site and the entire B23 cDNA. The primers for PCR are designed so that they create XbaI sites in the product. The PCR product is then digested with the XbaI restriction endonuclease and the product ligated into the linearized pREP4 plasmid. The pQE-30 vector codes for a 6 histidine sequence (His-tag) on the N-terminal end of the protein. Therefore, it may be desirable to remove this sequence from the plasmid coding for B23. The advantage of this would be that only the recombinant protein of interest would contain the His-tag, facilitating selective purification of the recombinant protein by the nickel chelating column system provided by Qiagen. Deletion of the His-tag coding sequence may be achieved by a technique called splicing by overlap extension, or SOEing (Horton and Pease, 1991), using two additional primers and an additional round of PCR prior to insertion into the pREP4 plasmid. The new construct with the B23 cDNA inserted into the pREP4 plasmid is then used to transform either strain M15 or SG13009 of E coli. The transformed bacteria is then ready for transformation with a pQE vector into which the cDNA for the desired protein has been inserted. Expression is achieved by methods described in the manual supplied with the Qiagen kit.

Method 2: expression of a bicistronic message from a single plasmid—Method 2 also utilizes the Qiagen system for expression, but both the cDNA for the protein of interest and the B23 cDNA are placed in one of the pQE expression plasmid vectors; e.g., pQE-30. The cDNA for the protein of interest is inserted into plasmid pQE-30 at one of the restriction sites in the first half of the multiple cloning site. The plasmid is then propagated and digested with restriction endonuclease Hind III. The source of the cDNA for protein B23 is a plasmid construct in which the B23 cDNA has been inserted into the vector pET11c from Novagen (Szebeni et al., 1997). In this case, primers are designed so that the sequence containing the ribosome binding site and the cDNA are amplified by PCR. The primers also introduce Hind III sites in the PCR product. After amplification the PCR product is digested with the Hind III restriction endonuclease and the product ligated into the linearized pQE-30 plasmid which already contains the protein of interest. The resulting product is then used to transform either E. coli strain M15[pREP4] or SG13009[pREP4], and is then used for expression as indicated by the manual supplied with the Qiagen kit.

Tests for effects of co-expression on inclusion body formation—Although many proteins form inclusion bodies in E. coli when expressed as recombinant protein, two examples will be considered here. Green fluorescent protein (GFP) has been shown to form inclusion bodies when expressed at high levels (Reid and Flynn, 1997). Dihydrofolate reductase (DHFR) also forms inclusion bodies and a vector for its expression (pQE-40) is available from Qiagen. Both of these proteins may be used as test substrates for determining the effects of B23 co-expression on inclusion body formation. The proteins are expressed in E. coli either alone or together with protein B23 as described above.

Two effects are measured: 1) solubility of the recombinant protein after expression and cell lysis and 2) total yield of expressed protein. The bacterial cultures are grown in pairs with one group containing the B23 expression plasmid plus the plasmid for the other recombinant protein and the second containing only the latter plasmid. After lysis, equivalent aliquots of the supernatant and pellet are applied to SDS-PAGE gels and analyzed for relative amounts of expressed protein. This can be quantified by scans of the gels on a scanner. The relative amounts of recombinant protein extracted into the supernatant will be compared for the samples with or without B23 co-expression. Secondly, the overall yield of protein is compared in SDS lysates of bacteria as above. By using these methods, increases both in soluble protein and in total protein expressed may be obtained for difficult-to-express proteins when protein B23 is co-expressed with the recombinant protein.

Protein purification—The recombinant protein of interest is purified by the following general scheme. After bacterial co-expression of the recombinant protein and protein B23 using either of the systems described above, the bacteria is lysed and the lysate applied to a nickel-nitrilotriacetic acid (NTA) agarose column (Qiagen). The unbound proteins are allowed to pass through the column and the bound protein of interest is eluted with imidazole. In most cases, the recombinant protein and B23 remain associated during the purification process and elute from the column as a complex. Therefore, another step is required to separate protein B23 from the protein of interest. Dissociation of the complex is achieved by phosphorylating with the enzyme casein kinase 2 (CK2). The general protocol for this is described elsewhere in the Examples. After treatment with CK2, the mixture is applied to another column of NTA-agarose. In this case the protein of interest binds the column, whereas protein B23 and CK2 pass through the column. The protein of interest is then eluted with imidazole and subjected to further steps of purification, if necessary.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

Throughout this application, various publications are referenced. The disclosures of these publications, and the references cited therein, in their entireties are hereby incorporated by reference into this application in order to more fully describe the state of the art to which this invention pertains.

REFERENCES

Anson M L, & Schirmer E W, (1963) *J Biol Chem* 238, 3884–3891.
Birnboim H C, (1983) *Meth Enzymol* 100, 243–255.
Borer R A, Lehner C F, Eppenberger H M, Nigg E A. (1989) *Cell* 56 :379–390.
Biggiogera M, et al., (1990) *Development* 110, 1263–1270.
Bradford M M, (1976) *Anal Biochem* 72, 248–254.
Buchner J, (1996) *FASEB J* 10, 10–19.
Buchner J B, Grallert H, Jacob U, (1998) *Meth Enzymol* 290, 323–338.
Busch H, Smetana K. 1970. *The Nucleolus*. Academic Press, New York.
Campbell K S et al., (1997) *Genes & Development* 11:1098–110.
Chan W Y, et al. (1989) *Biochemistry* 28, 1033–1039.
Chang J H, & Olson M O J, (1989) *J Biol Chem* 264, 11732–11737.
Chan P K, & Chan F Y, (1995) *Biochim Biophys Acta* 126, 37–42.
Chang J H, Dumbar T S, & Olson M O J, (1988) *J Biol Chem* 263, 12824–12837.
Chang J H, Lin J Y, Wu M H, Yung B Y M. (1998) *Biochem J* 329:539–544.
Chang J-H, & Olson M O J, (1990) *J Biol Chem* 265, 18227–18233.
Cole P A, (1996) *Structure* 4, 239–242.
Dayhoff et al., (1978) *Atlas of Protein Sequence and Structure.* Nat'l. Biomed. Res. Found., Washington, D.C.
Eichler D C, Craig N. (1994) *Prog. Nucleic Acid Res and Mol Biol* 49:197–239.
Ellis R J. 1997. Molecular chaperones: avoiding the crowd. *Curr Biol* 7:R531–R533.
Fankhauser C, et al. (1991) *Mol Cell Biol* 11:2567–2575.
Fedorov A N. Baldwin T O. (1997) *J Biol Chem* 272:32715–32718.
Feuerstein N, & Mond J J, (1987) *J Immunol* 139, 1818–1822.
Goldfarb D S. (1988) *Cell Biol Intern Rep* 128:809–832.
Guagliardi A, Cerchia L, & Rossi M, (1995) *J Biol Chem* 270, 28126–28132.
Hadjiolov A A. 1984. *The Nucleolus and Ribosome Biogenesis.* Springer-Verlag, New York.
Hendrick J P, & Hartl F-U, (1995) *FASEB J* 9, 1559–1569.
Herrera J E, Savkur R, & Olson, M O J, (1995) *Nucleic Acids Res* 23, 2974–3979.
Herrera J E, Correia J J, Jones A E, & Olson M O J, (1996) *Biochemistry* 35, 2688–2673.
Horton R M & Pease L R, (1991) in *Directed Mutagenesis, A Practical Approach* (M. J. McPherson, ed.) pp. 217–247, IRL Press.
Jakob U, Buchner J. (1994) *Trends Biochem Sci* 19:205–211.
Jakob U et al. (1993) *J Biol Chem* 268:1517–1520.
Jaenicke R, Rudolph R. (1990) Folding proteins. In: Creighton T E. ed. *Protein structure a practical approach.* IRL Press at Oxford University Press. pp. 191–223.
Karn et al., (1995) In: Karn, J., eds., *HIV a practical approach, biochemistry, molecular biology and drug discovery,* Vol. 2, Oxford, UKL IRL Press, pp. 147–165.
Knittler M R, & Haas I G, (1992) *EMBO J* 11, 1573–1581.
Laskey R A, Honda B M, & Finch J T, (1978) *Nature* (London) 275, 416–420.
Li Y-P, et al. (1996) *Eur J Biochem* 237:153–158.
Lui C-P, Chan P-K, Fung K-P, Choy Y-M & Lee C-Y, (1993) *Cancer Lett* 70, 129–139.
Maier G, Dietrich U, Panhans B, Schroeder B, Ruebsamen-Waigmann H, Cellai L, Hermann T & Heumann H, (1999) *Eur J Biochem* 261, 10–18.
Martin J, et al. (1991) *Nature* 352:36–42.
Mock D M, Lankford G, Horowitz P. (1988) *Biochim Biophys Acta* 956:23–29.
Moss T, Stefanovsky V Y. (1995) *Prog Nucleic Acid Res and Mol Biol* 50:25–66.
Muchowski P J, et al. (1997) *J Biol Chem* 272, 2578–2582.
MacArthur C A, & Shackleford G M, (1997) *Genomics* 42, 137–140.
Norcum M. (1996) *Protein Sci* 5:1366–1375.
Olson M O J. (1990) The role of proteins in nucleolar structure and function. In: Strauss P R. Wilson S. H. eds. *The Eukaryotic Nucleus: Molecular Biochemistry and Macromolecular Assemblies.* West Caldwell, N.J.: Telford Press. Vol 2, pp. 541–546.
Olson M O J, et al. (1986) *Biochemistry* 25:484–491.
Peculis B, & Gall J, (1992) *J Cell Biol* 116, 1–14.
Reid B G & Flynn G C, (1997) *Biochemistry* 36, 6786–6791.
Ruddon R W, & Bedows E, (1997) *J Biol Chem* 272, 3125–3128.
Sambrook et al. 1989. *Molecular Cloning: A Laboratory Manual,* 2d Ed., Cold Spring Harbor Laboratory Pres, Cold Spring Harbor, N.Y.
Schmidt-Zachmann M S, Hugle-Dorr B, & Franke W, (1987) *EMBO J* 6, 1881–1890.
Shan X, Xue Z, Melese T. (1994) *J Cell Biol* 126:853–862.
Spector D L, Ochs R L, & Busch H, (1984) *Chromosoma* 90, 139–148.
Szebeni A, Herrera J E, Olson M O J, (1995) *Biochemistry* 34 :8037–8042.
Szebeni A, et al., (1997) *Biochemistry* 36: 8037–8042.
Szebeni A, & Olson M O J, (1999) *Protein Science* 8, 905–912.
Taguchi T, & Yoshida M, (1998) *Meth Enzymol* 290, 169–180.
Theopold U, Dal Zotto L, Hultmark D. (1995) *Gene* 156: 247–251.
Umekawa H, et al.(1993) *Cell and Mol Biol Res* 39, 635–645.
Valdez B C, et al. (1994) *J Biol Chem* 269:23776–23783.
Wang D, Umekawa H, & Olson M O J, (1993) *Cell & Mol Biol Res* 39, 33–42.
Wang D, Baumann A, Szebeni A, & Olson M O J, (1994) *J Biol Chem* 269, 30994–30998.
Warner J R. (1990) *Current Opinion in Cell Biology* 2:521–527.
Welch W J, Feramisco J R (1984) *J Biol Chem* 259:4501–4513.
Wiech H, Buchner J, Zimmermann R, Jakob U. (1992) *Nature* 358:169–170.
Wingfield et al. (1991) *Biochemistry* 30: 7527–7534.
Zimmerman S B, Minton A P. (1993) *Ann Rev Biophys Biomol Struct* 22 :27–65.
Zirwes R E, et al. (1997) *Mol Biol Cell* 8, 231–248.

What is claimed is:

1. A method of preventing aggregation of a protein, comprising contacting a solution containing the protein with nucleolar protein B23, thereby preventing aggregation of the protein.

2. A method of maintaining solubility of a protein, comprising contacting a solution containing the protein with nucleolar protein B23, thereby maintaining solubility of the protein.

3. The method of claim 1 or 2, wherein the protein is selected from the group consisting of HIV-1 Rev protein, liver alcohol dehydrogenase, carboxypeptidase A, citrate synthase, carbonic anhydrase, and rhodanese.

4. A method of preventing aggregation of and maintaining solubility of a protein during thermal denaturation, comprising contacting the protein with nucleolar protein B23 while subjecting the protein to thermal denaturation, thereby preventing aggregation of and maintaining solubility of the protein.

5. The method of claim 4, wherein the selected protein is selected from the group consisting of HIV-1 Rev protein, liver alcohol dehydrogenase, carboxypeptidase A, citrate synthase, carbonic anhydrase, and rhodanese.

6. A method of maintaining solubility of an expressed recombinant protein in a recombinant protein-expressing bacterium, comprising transforming the bacterium with a vector that expresses the recombinant protein and a vector that expresses nucleolar protein B23, whereby the recombinant protein and B23 are in contact.

7. The method of claim 6, wherein the vector that expresses the recombinant protein and the vector that expresses nucleolar protein B23 are the same vector.

8. A method of reactivating a protein that has been inactivated by thermal denaturation, comprising contacting the protein with nucleolar protein B23.

9. A method of reactivating a protein that has been inactivated by contact with a chemical denaturant, comprising:

a) ending contact between the protein and the chemical denaturant; and b) contacting the protein with nucleolar protein B23.

* * * * *